(12) United States Patent
Tanaka et al.

(10) Patent No.: US 9,445,733 B2
(45) Date of Patent: Sep. 20, 2016

(54) ELECTRONIC DEVICE

(71) Applicant: Seiko Epson Corporation, Shinjuku-ku (JP)

(72) Inventors: Shigemitsu Tanaka, Okaya (JP); Yoshihiro Hidai, Shiojiri (JP); Junya Shibuya, Azumino (JP)

(73) Assignee: Seiko Epson Corporation, Tokyo (JP)

( * ) Notice: Subject to any disclaimer, the term of this patent is extended or adjusted under 35 U.S.C. 154(b) by 128 days.

(21) Appl. No.: 14/207,116

(22) Filed: Mar. 12, 2014

(65) Prior Publication Data

US 2014/0268522 A1 Sep. 18, 2014

(30) Foreign Application Priority Data

Mar. 18, 2013 (JP) ................. 2013-054685
Mar. 18, 2013 (JP) ................. 2013-054686

(51) Int. Cl.
| | |
|---|---|
| *H05K 7/00* | (2006.01) |
| *H05K 5/00* | (2006.01) |
| *A61B 5/0295* | (2006.01) |
| *A61B 5/00* | (2006.01) |
| *A61B 5/02* | (2006.01) |
| *A61B 5/16* | (2006.01) |

(52) U.S. Cl.
CPC ............ *A61B 5/0295* (2013.01); *A61B 5/681* (2013.01); *A61B 5/683* (2013.01); *A61B 5/02007* (2013.01); *A61B 5/165* (2013.01); *A61B 5/6823* (2013.01); *A61B 5/6824* (2013.01); *A61B 2560/0406* (2013.01); *A61B 2562/146* (2013.01); *A61B 2562/18* (2013.01); *A61B 2562/185* (2013.01)

(58) Field of Classification Search
CPC .................................. A63B 23/0244
USPC ....................... 361/679.01–679.03
See application file for complete search history.

(56) References Cited

U.S. PATENT DOCUMENTS

| | | | | |
|---|---|---|---|---|
| 5,522,401 | A | * 6/1996 | Brucker | ............ A63B 23/0244 482/148 |
| 2008/0097221 | A1* | 4/2008 | Florian | ............ A61B 5/02433 600/476 |

FOREIGN PATENT DOCUMENTS

| | | |
|---|---|---|
| JP | 2007-285743 A | 11/2007 |
| JP | 2009-066356 A | 4/2009 |
| JP | 2010-137110 A | 6/2010 |

* cited by examiner

*Primary Examiner* — Jerry Wu
(74) *Attorney, Agent, or Firm* — Kilpatrick Townsend & Stockton LLP

(57) ABSTRACT

An electronic device is an electronic device that measures biological information. The electronic device includes a biological-information sensor section configured to measure the biological information and an armor case configured to house the biological-information sensor section. The armor case includes a case main body section and a rear lid section. One surface of the case main body section is integrally molded with a windshield and the other surface of the case main body section is formed of a transparent member in which an opening section is formed. The rear lid section is attached to the case main body section to close the opening section and at least a part of the rear lid section is formed of a transparent member.

20 Claims, 15 Drawing Sheets

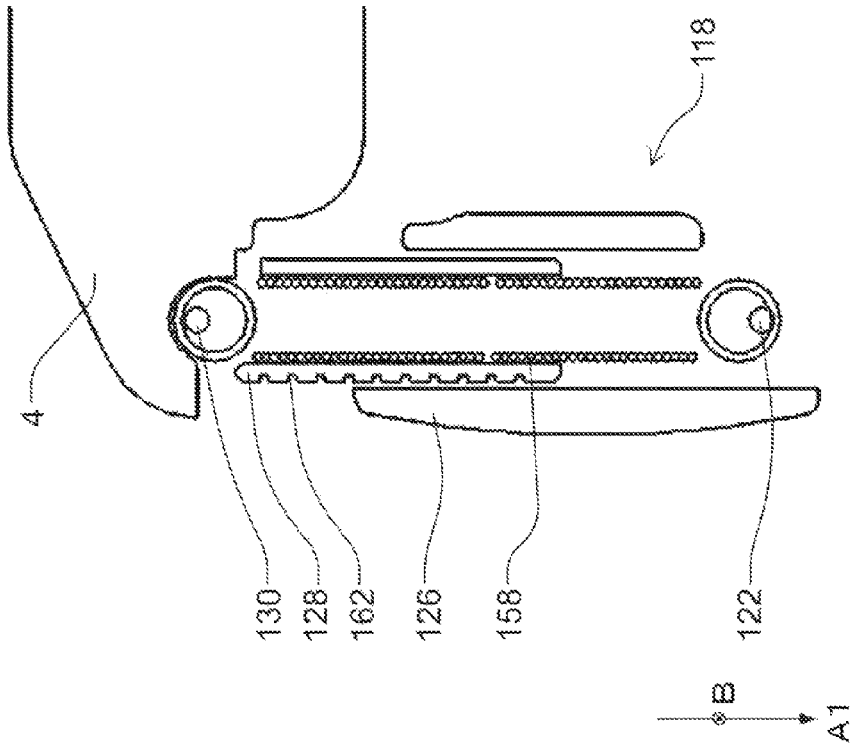
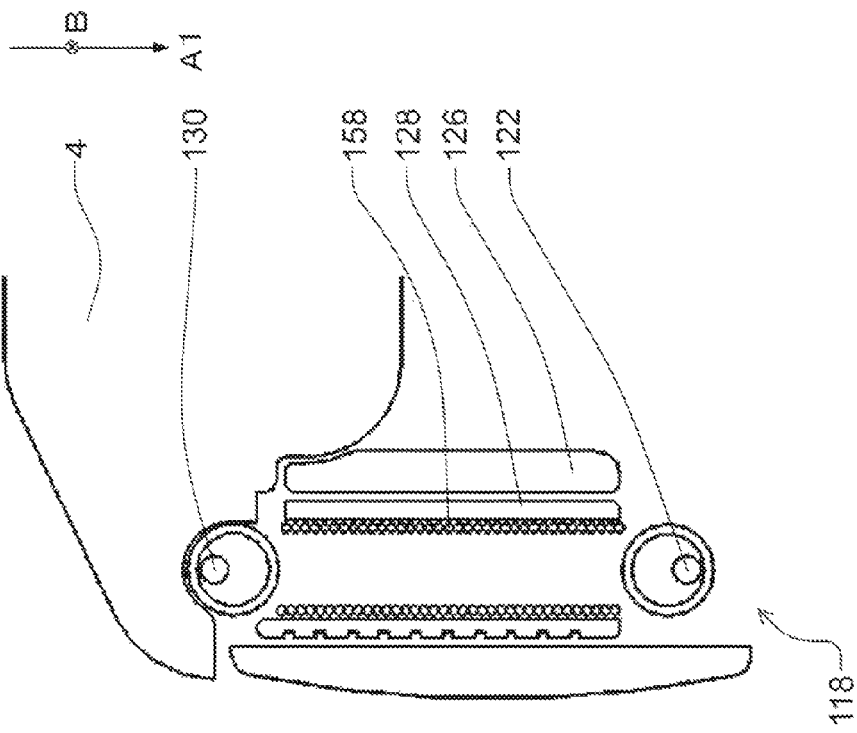

ELECTRONIC DEVICE

This application claims priority to Japanese Patent Application No. 2013-054685, filed Mar. 18, 2013 and Japanese Patent Application No. 2013-054686, filed Mar. 18, 2013, the entirety of which is hereby incorporated by reference.

BACKGROUND

1. Technical Field

The present invention relates to an electronic device.

2. Related Art

In recent years, a large number of electronic devices including display sections are reduced in size and thickness in order to improve portability and designability. Most display sections used in electronic devices such as a watch are susceptible to a peripheral environment and are delicate. Therefore, to enable stable and long-period use of a display section, the display section is sometimes housed in a housing in which the inner peripheral wall of a time display window and the side surfaces of a windshield glass are set in close contact with each other via a gasket (see, for example, JP-A-2007-285743 (Patent Literature 1)).

However, in the configuration including the gasket disclosed in Patent Literature 1, the housing needs to have rigidity because the gasket is pressed with strong force. As an example of a method of securing necessary rigidity, a metal material having high rigidity is adopted as the housing. However, this causes influences on the weight of the electronic device and a communication radio wave and an increase in costs and makes it difficult to inexpensively provide the electronic device. As another example of the method, the housing is increased in thickness. However, when this method is adopted, the size of the housing of the electronic device increases and, in particular, the thickness of the housing increases. Therefore, it is likely that this makes it difficult to maintain reductions in size, thickness, and weight of the electronic device and improve waterproof performance.

SUMMARY

An advantage of some aspects of the invention is to solve at least a part of the problems described above, and the invention can be implemented as the following forms and application examples.

Application Example 1

This application example is directed to an electronic device that measures biological information, the electronic device including: a biological-information sensor section configured to measure the biological information; and an armor case configured to house the biological-information sensor section. The armor case includes: a case main body section; and a rear lid section. One surface of the case main body section is integrally molded with a windshield and the other surface of the case main body section is formed of a transparent member in which an opening section is formed. The rear lid section is attached to the case main body section to close the opening section and at least a part of the rear lid section is formed of a transparent member.

According to this application example, it is possible to integrate the case main body section and the windshield in a general structure and eliminate a leakage along contact surface of moisture and high-pressure gas in a contact surface section between the case main body section and the windshield and a penetration leakage of the moisture and the high-pressure gas that leak penetrating through an internal texture of a windshield gasket. Consequently, it is unnecessary to take into account rigidity design for securing a waterproof property of the contact surface section between the case main body section and the windshield. Therefore, it is possible to maintain reduction in size, thickness, and weight of the electronic device and improve waterproof performance. Compared with fixing of the windshield by welding, the influence on the waterproof property due to fluctuation in welding quality does not have to be considered. Since a welding and fixing process is unnecessary, there is also a cost merit.

The "transparent member" of the case main body section means a member for transmitting visible light and may be either colored and transparent or colorless and transparent (however, in order to increase the transmittance of the visible light, the transparent member is preferably colorless and transparent). The "transparent member" of the rear lid section means a member for transmitting light used in the biological-information sensor section and may be either colored and transparent or colorless and transparent.

Application Example 2

This application example is directed to the electronic device according to the application example described above, wherein the armor case is provided with a protector for blocking light to cover the case main body section excluding at least the windshield.

According to this application example, it is possible to suppress intrusion of light, which causes measurement noise, into the biological-information sensor section. Further, it is possible to maintain reductions in size, thickness, and weight of the electronic device and improve waterproof performance while securing measurement performance for biological information. Therefore, the electronic device has a suitable configuration.

Application Example 3

This application example is directed to the electronic device according to the application example described above, wherein the protector includes a first engaging section and a second engaging section for engaging the armor case and a band section.

According to this application example, it is possible to suppress the influence on biological information measurement while securing easiness of dress-up of the protector.

Application Example 4

This application example is directed to the electronic device according to the application example described above, wherein the electronic device further includes a panel cover having a light transmission area smaller than the windshield in a projection view in a direction from the case main body section to the rear lid section.

According to this application example, it is possible to suppress external light entering from the windshield or the vicinity of the contact surface section between the case main body section and the windshield from intruding into the inside of the electronic device and causing measurement noise of the biological-information sensor section. Therefore, the electronic device has a suitable configuration.

Application Example 5

This application example is directed to the electronic device according to the application example described above, wherein the rear lid section further includes a detection window, and the electronic device further includes a light-guide control section configured to extend from the rear lid section to the case main body section and block light formed around the detection window.

According to this application example, even when the case main body section is formed of a transparent material, it is possible to suppress intrusion of light, which causes measurement noise, into the biological-information sensor section. Therefore, the electronic device has a suitable configuration.

Application Example 6

This application example is directed to the electronic device according to the application example described above, wherein the rear lid section is formed by two-color molding.

According to this application example, the transparent member and the other parts of the rear lid section are integrally formed by the two-color molding. Therefore, it is possible to reduce the number of components. Further, it is possible to form the rear lid section easily and at low costs.

Application Example 7

This application example is directed to the electronic device according to the application example described above, wherein at least a part of the detection window is formed to project in a direction from the case main body section to the rear lid section.

According to this application example, for example, when the electronic device is mounted on the wrist of a user and used, the biological-information sensor section is pressed against the wrist with a proper pressing force and biological information measurement in a stable state can be performed. Therefore, it is possible to accurately measure biological information.

Application Example 8

This application example is directed to the electronic device according to the application example described above, wherein the biological-information sensor section includes a photo-sensor.

According to this application example, in the electronic device, the biological-information sensor section includes the photo-sensor. Therefore, with a characteristic of the photo-sensor, it is possible to accurately measure, for example, a pulse as biological information.

Application Example 9

This application example is directed to the electronic device according to the application example described above, wherein the band section includes: a first band member and a second band member attached to a device main body of the electronic device; and a coupling member provided at the end on the opposite side of the device main body in the first band member and configured to couple the first band member and the second band member, at least one of the first band member and the second band member includes an expandable section configured to expand and contract along a band extending direction, which is an extending direction from the device main body, and the expandable section includes: a first fitting member located on the device main body side; a second fitting member provided to be displaceable with respect to the first fitting member along the band extending direction; and an urging member housed in the first fitting member and the second fitting member and configured to urge the second fitting member in the opposite direction of the band extending direction.

According to this application example, the second fitting member is relatively displaced along the band extending direction of the band members with respect to the first fitting member supported by the device main body of the electronic device. The urging member arranged between the first fitting member and the second fitting member urges the second fitting member in the opposite direction of the band extending direction. Consequently, since the first fitting member is provided relatively to the movement of the second fitting member, it is possible to suppress movement in an unintended direction of the second fitting member.

Application Example 10

This application example is directed to the electronic device according to the application example described above, wherein one of the first fitting member and the second fitting member includes a display section configured to display a displacement amount of the second fitting member.

According to this application example, examples of a component for displaying the displacement amount of the second fitting member can include a scale and a mark. The displacement amount of the second fitting member can be checked using the display section. It is possible to confirm, with reference to the displacement amount, that a proper tensile force is acting on the band section the device main body is mounted on a human body with appropriate pressure.

Application Example 11

This application example is directed to the electronic device according to the application example described above, wherein one of the first fitting member and the second fitting member includes a convex section formed along a displacement direction of the second fitting member.

According to this application example, the displacement of the second fitting member is guided by the convex section. Therefore, it is possible to stably displace the second fitting member.

Application Example 12

This application example is directed to the electronic device according to the application example described above, wherein one of the first fitting member and the second fitting member is a male fitting member and the other is a female fitting member.

According to this application example, one of the first fitting member and the second fitting member is the male fitting member and the other is the female fitting member. Therefore, it is possible to extremely easily specify the position of the second fitting member with respect to the first fitting member.

Application Example 13

This application example is directed to the electronic device according to the application example described above, wherein the expandable section is configured to be pivotable around a fitting section between the device main body and the first fitting member.

According to this application example, the expandable section is configured to be pivotable. Therefore, it is possible to cope with a difference in the thickness of an arm of a human body.

Application Example 14

This application example is directed to the electronic device according to the application example described above, wherein the expandable section includes a drawing spring.

According to this application example, it is possible to secure an initial load, reduce a spring constant, and save a space by using the drawing spring.

Application Example 15

This application example is directed to the electronic device according to the application example described above, wherein the device main body comes into contact with a human body and measures the biological information.

According to this application example, the urging member urges, in the opposite direction of the band extending direction of the band members, the second fitting member displaced relatively to the first fitting member when the electronic device is mounted on the human body. Therefore, when the electronic device is mounted on the human body, it is possible to additionally tighten the band together with the expandable section. Therefore, it is possible to appropriately mount the electronic device on the human body. It is possible to attain an effect same as the effect of the band. Consequently, it is possible to stably perform measurement of biological information by the device main body. Further, it is possible to improve accuracy of the measurement.

Application Example 16

This application example is directed to the electronic device according to the application example described above, wherein the device main body includes a stopper configured to limit pivoting of the first fitting member with respect to the device main body.

According to this application example, the pivoting of the first fitting member with respect to the device main body is limited by the stopper. Therefore, an impact on a part (e.g., glass) of the rear surface of the device main body due to a fall or the like is reduced.

BRIEF DESCRIPTION OF THE DRAWINGS

The invention will be described with reference to the accompanying drawings, wherein like numbers reference like elements.

FIGS. 4A to 4C are diagrams showing an armor case according to this embodiment, wherein FIG. 4A is a rear view, FIG. 4B is a front view, and FIG. 4C is a side view.

FIGS. 8A and 8B are perspective views showing the biological information measurement device according to the embodiment, wherein FIG. 8A is a diagram showing a state of an expandable section before displacement of a second fitting member and FIG. 8B is a diagram showing a state of the expandable section after the displacement of the second fitting member.

FIGS. 9A and 9B are side views showing the biological information measurement device according to the embodiment, wherein FIG. 9A is a diagram showing a state of the expandable section before the displacement of the second fitting member and FIG. 9B is a diagram showing a state of the expandable section after the displacement of the second fitting member.

FIGS. 12A and 12B are perspective views showing expanding and contracting states of the expandable section according to the embodiment, wherein FIG. 12A is a diagram showing a state of the expandable section before the displacement of the second fitting member and FIG. 12B is a diagram showing a state of the expandable section after the displacement of the second fitting member.

FIGS. 13A and 13B are sectional views showing expanding and contracting states of the expandable section according to the embodiment, wherein FIG. 13A is a diagram showing a state of the expandable section before the displacement of the second fitting member and FIG. 13B is a diagram showing a state of the expandable section after the displacement of the second fitting member.

FIGS. 18A and 18B are perspective views showing expanding and contracting states of an expandable section according to a modification 1, wherein FIG. 18A is a diagram showing a state of the expandable section before displacement of a second fitting member and FIG. 18B is a diagram showing a state of the expandable section after the displacement of the second fitting member.

DESCRIPTION OF EXEMPLARY EMBODIMENTS

An embodiment of the invention is explained below with reference to the drawings. Note that the drawings referred to below is enlarged or reduced as appropriate to enable recognition of a part being explained.

Schematic Configuration of a Biological Information Measurement Device

Figure 1:
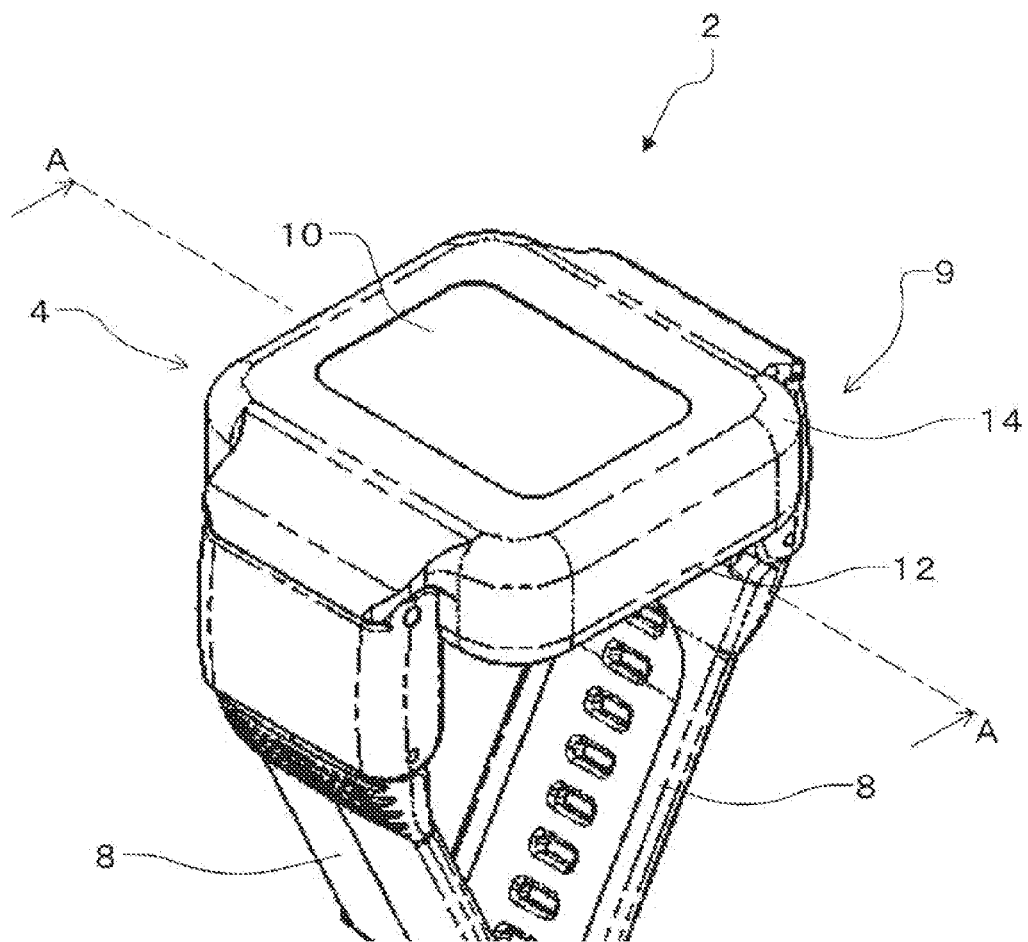
FIG. 1 is a perspective view showing a biological information measurement device according to an embodiment.
Figure 2:
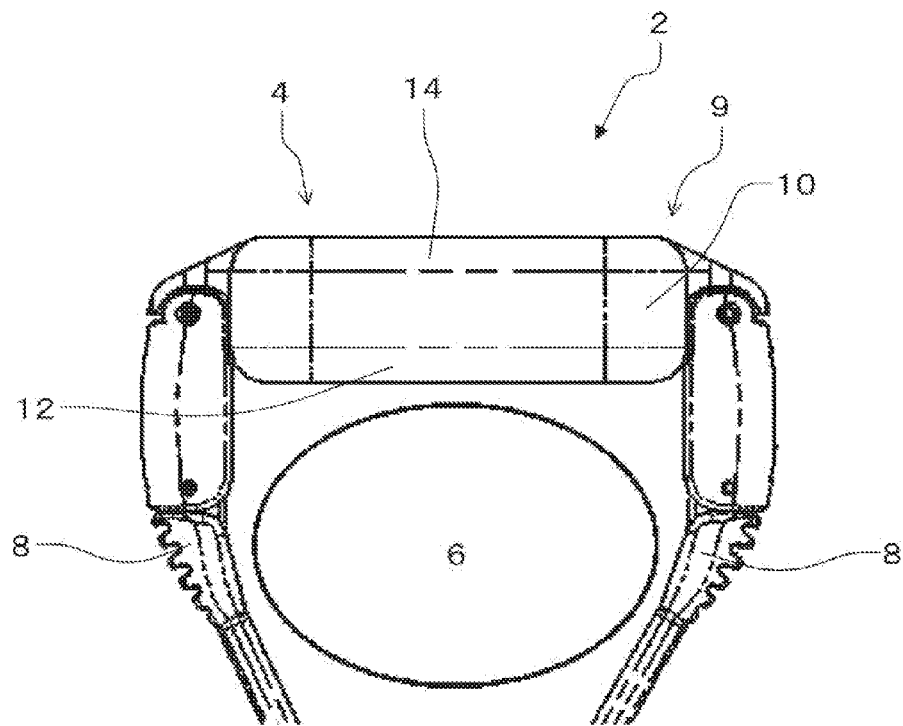
FIG. 2 is a side view showing the biological information measurement device according to the embodiment.

FIG. 1 is a perspective view showing a biological information measurement device 2 according to this embodiment. FIG. 2 is a side view showing the biological information measurement device 2 according to this embodiment. Note that data display and operation buttons and the like are not shown in the figures.

The biological information measurement device 2 according to this embodiment is an electronic device mounted on a human body, for example, a wrist 6 to measure biological information such as a pulse wave. The biological information measurement device 2 includes a device main body 4 brought into close contact with the human body to measure biological information and a pair of band sections 8 attached to the device main body 4 to mount the device main body 4 on the wrist 6.

The device main body 4 includes a case main body section 10, a rear lid section 12, and a protector 14. The case main body section 10, the rear lid section 12, and the protector 14 configure an armor case 9.

Figure 3:
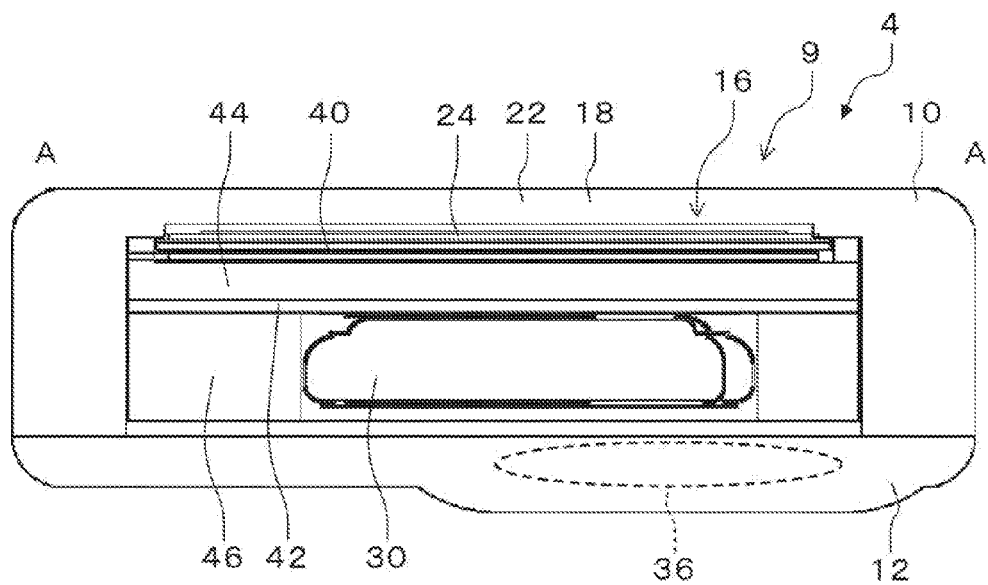
FIG. 3 is a sectional view taken along line A-A in FIG. 1.

FIG. 3 is a sectional view taken along line A-A in FIG. 1. The device main body 4 includes a module 16. The module 16 includes a pulse sensor section 36 functioning as a biological-information sensor section configured to measure a pulse wave as biological information, a display panel 24, an EL (Electro Luminescence) panel 40 for illumination, a circuit board 42, a panel frame 44, a circuit case 46, and a battery 30.

The pulse sensor section 36 includes a photo-sensor (a photoelectric sensor). Consequently, since the pulse sensor section 36 includes the photo-sensor, the biological information measurement device 2 can measure, with characteristics of the photo-sensor, for example, a pulse wave as biological information and derive a pulse rate, the hardness of a blood vessel, a state concerning exercise, a psychological state, and the like on the basis of the pulse wave.

The photo-sensor condenses, with a condensing mirror, light irradiated from a light-emitting element such as an LED (Light Emitting Diode) toward the wrist 6 of a user and reflected on a blood vessel of the wrist 6 and receives the light in a light-receiving element such as a photodiode. In receiving the light, the photo-sensor measures a pulse of the user making use of a phenomenon in which the reflectance of the light is different during expansion and during contraction of the blood vessel. Therefore, the pulse sensor section 36 is preferably pressed against the wrist 6 and more preferably brought into close contact with the wrist 6 to prevent light, which causes measurement noise, from being received by the light-receiving element of the photo-sensor.

The panel frame 44 for guiding the display panel 24, the EL panel 40, and the like is arranged on one surface of the circuit board 42 and the circuit case 46 for guiding the battery 30 and the like is arrange on the other surface.

Note that, as the circuit board 42, for example, a substrate of epoxy resin including glass fiber is used. Wiring patterns formed of a copper foil or the like are formed on both the surfaces of the circuit board 42. Resin such as polyacetal or polycarbonate is used for the panel frame 44 and the circuit case 46.

On the circuit board 42, components configuring a circuit for driving the photo-sensor and measuring a pulse, a circuit for driving the display panel 24, a circuit for controlling the circuits, and the like are mounted. An electrode for connection to the display panel 24 is formed on one surface of the circuit board 42. The electrode for connection is conducted to an electrode of the display panel 24 via a not-shown connector. As the display panel 24, a display member such as a liquid crystal panel is used. Pulse measurement data such as a pulse rate, time information such as present time, and the like are displayed on the display panel 24 according to modes. The EL panel 40 is arranged between the display panel 24 and the panel frame 44 and connected to the circuit board 42. The EL panel 40 is lit by predetermined operation of operation buttons 26 by the user to illuminate the display panel 24.

As the battery 30 housed in the circuit case 46, a rechargeable button-type lithium secondary battery is used. Terminals of both poles of the battery 30 are connected to the circuit board 42 to supply electric power to a circuit for controlling a power supply. The electric power is, for example, converted into a predetermined voltage by the circuit and supplied to the circuit for driving the photo-sensor and measuring a pulse, the circuit for driving the display panel 24, the circuit for controlling the circuits, and the like and actuates the circuits.

The battery 30 is charged via a pair of charging terminals 32 conducted to the circuit board 42 by a conduction member such as a coil spring. Note that, as the battery 30, a primary battery that does not need to be charged may be used.

Figure 4:
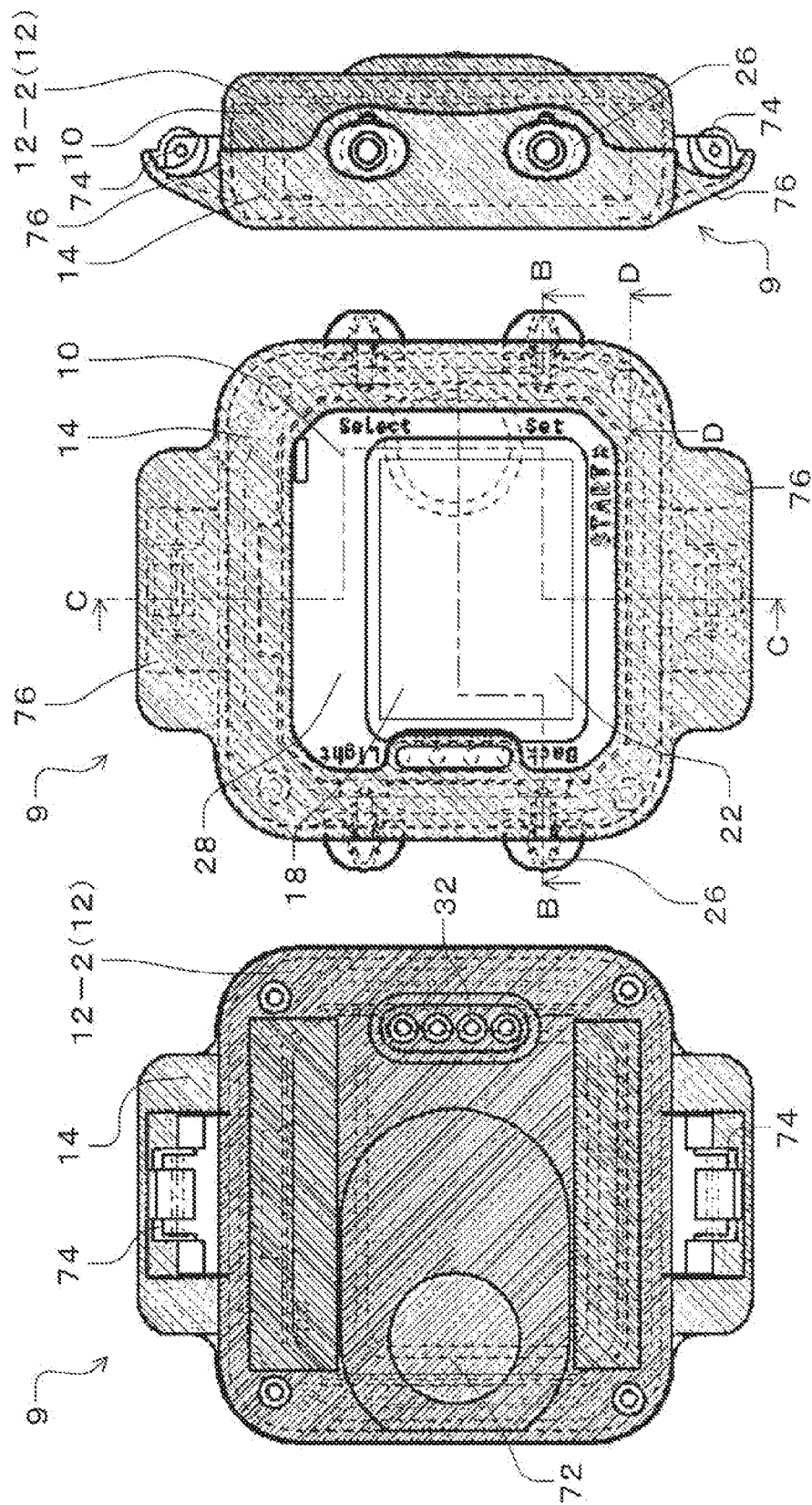
Figure 5:
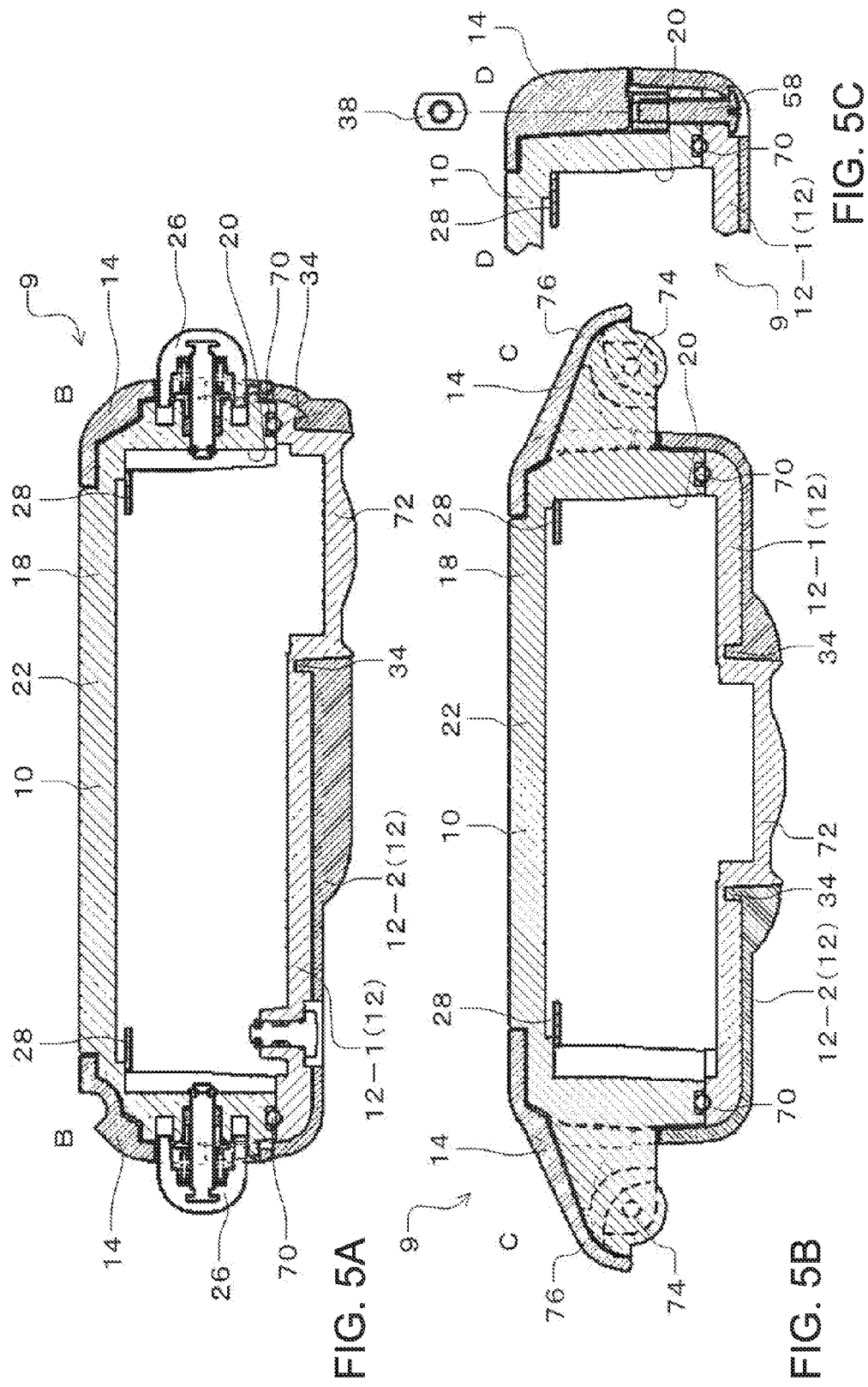
FIG. 5A is a sectional view taken along line B-B in FIG. 4B.
FIG. 5B is a sectional view taken along line C-C in FIG. 4B.
FIG. 5C is a sectional view taken along line D-D in FIG. 4B.

FIGS. 4A to 4C are diagrams showing the armor case 9 according to this embodiment. FIG. 4A is a rear view, FIG. 4B is a front view, and FIG. 4C is a side view. FIG. 5A is a sectional view taken along line B-B in FIG. 4B. FIG. 5B is a sectional view taken along line C-C in FIG. 4B. FIG. 5C is a sectional view taken along line D-D in FIG. 4B.

In this embodiment, one surface of the case main body section 10 is integrally molded with a windshield 18. An opening section 20 is formed on the other surface. The case main body section 10 is molded using transparent acrylic resin or transparent polycarbonate.

In the case main body section 10, a data display window section 22 for displaying pulse measurement data and the like is formed on the opposite side of the rear lid section 12 side. The display panel 24 (see FIG. 3) for displaying pulse measurement data and the like can be visually recognized from the data display window section 22.

In the data display window section 22, the windshield 18 integrally molded with the case main body section 10 from transparent resin or the like is provided. The display panel 24 is protected by the windshield 18. A frame-like panel cover 28, on which functions of the operation buttons 26, a commodity logo, and the like are printed, is arranged below the outer periphery of the windshield 18. The panel cover 28 is provided around the inner side of the windshield 18 of the case main body section 10 in the front view of the armor case 9 in FIG. 4B (a projection view from the opposite direction of the opening section 20 of the case main body section 10 or a projection view from a display window side of the data display window section 22). In another expression, a light transmitting region (i.e., an opening region) of the panel cover 28 can be considered to have an area smaller than the area of the windshield 18. On the other hand, the panel cover 28 has a light transmission area equivalent to an area equal to or larger than a display region of the data display window section 22. Therefore, the panel cover 28 can block light entering from the windshield 18 or the periphery of a contact surface section between the case main body section 10 and the windshield 18 without spoiling visibility of the data display window section 22. Consequently, it is possible to suppress intrusion of light, which causes measurement noise, into the pulse sensor section 36 including the photo-sensor. In this embodiment, the panel cover 28 is configured by thin plate-like resin. However, a metal plate or the like may be used. The panel cover 28 is suitably colored in a color that easily absorbs or reflects light.

The case main body section 10 includes a plurality of the operation buttons 26 for performing various instructions for, for example, a mode change from a pulse measurement mode for displaying pulse measurement data to a normal mode for displaying present time or the like or a time correction mode for performing time correction and lighting of illumination. Note that, in this embodiment, the biological information measurement device 2 including four buttons is explained as an example. However, the number of buttons is not limited to this and may be one or two. If a touch panel is adopted as the display panel 24 and a material appropriate for the touch panel is selected as the material of the windshield 18, the operation explained above may be carried out using the touch panel without providing the buttons. In this case, since the number of components included in the biological information measurement device 2 decreases, it is possible to provide a more inexpensive device.

The rear lid section 12 is attached to the case main body section 10 to close the opening section 20 of the case main body section 10. An inner side 12-1 of the rear lid section is molded using transparent acrylic or polycarbonate. Waterproof performance is secured by holding a gasket between the rear lid section 12 and the case main body section 10. An outer side 12-2 of the rear lid section is formed of colored resin not to allow light to pass (not to show contents). The outer side 12-2 of the rear lid section is molded using colored polycarbonate, ABS resin, or the like. Further, strength of the surface of the outer side 12-2 of the rear lid section may be secured by covering the surface with a high-strength grade material including glass, carbon fiber, or the like.

For fixing the outer side 12-2 of the rear lid section and the inner side 12-1 of the rear lid section, for example, the outer side 12-2 and the inner side 12-1 are integrally molded by two-color molding (double mold) to secure, with both the materials of the outer side 12-2 and the inner side 12-1, thickness necessary for securing the strength of the rear lid section 12. Consequently, since a transparent member and the other parts of the rear lid section 12 are integrally molded by the two-color molding, it is possible to reduce the number of components and form the rear lid section 12 easily and at low costs. Further, it is possible to secure dimension accuracy by integrally molding the rear lid section 12. Consequently, it is possible to secure required waterproof performance (e.g., 5 atmospheres).

As shown in FIGS. 5A and 5B, the rear lid section 12 includes a light-guide control section 34 configured to block light. More specifically, the light-guide control section 34 extends from the rear lid section 12 toward the case main body section 10 and is formed around a detection window 72 (explained below). The light-guide control section 34 is formed around the detection window 72 of the rear lid section 12. With such a configuration, even if light that cannot be sufficiently blocked by the panel cover 28 or light intruding from a part not shielded by the protector 14 intrudes into the vicinity of the module 16 including the photo-sensor through a light guide formed by the transparent member of the rear lid section 12, it is possible to block the intruding light. Therefore, it is possible to suppress an influence on biological information measurement.

The detection window 72 provided in the rear lid section 12 is arranged to project to the outer side (the wrist 6 side, i.e., a direction from the case main body section 10 to the rear lid section 12) from the rear lid section 12. Note that a projection amount of the detection window 72 from the rear lid section 12 is preferably, for example, about 1 to 2 mm in order to secure a proper pressing force on the wrist 6. Consequently, when the biological information measurement device 2 is mounted on the wrist 6 of the user and used, a measurement part of the wrist 6 of the user is pressed by the detection window 72 with the proper pressing force and biological information measurement in a stable state can be performed. Further, if a part of the pulse sensor section 36, specifically, a light-emitting source, a light-receiving section, and the like are arranged in a space formed by the projection of the detection window 72 from the rear lid section 12, the distance between the pulse sensor section 36 and the measurement part of the wrist 6 of the user can be further reduced. Therefore, an amount of light reaching the pulse sensor section 36 increases and an S/N ratio can be improved. By arranging the detection window 72 provided in the rear lid section 12 to project to the outer side from the rear lid section 12 in this way, it is possible to improve measurement performance for biological information. Note that, in FIGS. 5A to 5C, the detection window 72 is unevenly arranged on the rear lid section 12. However, the detection window 72 is not limited to this. For example, the detection window 72 may be arranged in the vicinity of the center of the rear lid section 12.

In addition, a communication terminal for communicating with an external device and the pair of charging terminals 32 used in charging the battery 30, which is a power supply for the biological information measurement device 2, may be provided in the rear lid section 12.

In the biological information measurement device 2, a sealing member such as a gasket having a waterproof property is interposed between the case main body section 10 and the components incorporated in the case main body section 10, whereby the inside of the device main body 4 is hermetically sealed. That is, in a space formed by fitting the case main body section 10 and the rear lid section 12 such that opening sections thereof face each other, the module 16, the display panel 24, the panel cover 28, the battery 30, the biological-information sensor section 36, the EL panel 40, the circuit board 42, the circuit case 46, and the like are housed. The case main body section 10 and the rear lid section 12 are fit via a rear lid section gasket 70. Therefore, it is possible to secure waterproof performance. The biological information measurement device 2 can withstand use in water.

As shown in FIG. 4B, in the front view of the armor case 9 (a diagram of the armor case 9 viewed in a rear lid direction from the display surface side of the data display window section 22), the protector 14 is provided to cover the case main body section 10 excluding at least the windshield 18. In another expression, a light transmitting region (an opening area) of the protector 14 is smaller than a light transmitting region of the windshield 18. The armor case 9 includes the case main body section 10, the rear lid section 12, and the protector 14. Light transmitting regions respectively provided in the case main body section 10, the rear lid section 12, and the protector 14, i.e., regions of portions functioning as "windows", through which the inside of the device can be seen, are larger in the order of the case main body section 10, the protector 14, and the rear lid section 12. The protector 14 includes wing-like sections 76 for covering engaging sections 74 between the band sections 8 and the case main body section 10. The protector 14 protects the engaging sections 74 and, at the same time, blocks external light entering from a visual point direction shown in FIG. 4B. As shown in FIGS. 4C and 5B, the wing-like sections 76 also function as rotation limiting sections for keeping the rotation of the band sections 8 within a predetermined range. With this configuration, when the user removes the biological information measurement device 2 according to an embodiment of the invention from the arm and places the biological information measurement device 2 on a table, the band sections 8 do not spread wide. Therefore, since it is possible to prevent the rear lid side from coming into contact with the table, it is possible to prevent components important in biological information measurement such as the detection window 72 from being damaged.

FIG. 4A is a rear view of the armor case 9 (a diagram of the armor case 9 viewed in the direction of the windshield 18 from a side of the rear lid section 12 in contact with the human body). It is seen that, besides the detection window 72, the engaging sections 74 are not covered with light blocking members such as the protector 14 and the outer side 12-2 of the rear lid section. The engaging sections 74 are covered with the protector 14 in the front view (FIG. 4B). The band sections 8 are connected to the engaging sections 74. Therefore, the engaging sections 74 are not directly exposed to the external light. The external light does not intrude into the engaging sections 74. However, when the external light is, for example, reflected and indirectly intrudes from this part, the external light is blocked by the light-guide control section 34. Therefore, it is possible to suppress an adverse effect on biological information measurement. Note that it is desirable that a light transmitting region of the armor case 9 (an exposing area of the light transmitting member) in the rear view of FIG. 4A is smaller than the light transmitting region in the front view of FIG. 4B.

As shown in FIG. 5C, the protector 14 is fixed to the case main body section 10 after the rear lid section 12 is attached to the case main body section 10 in order to hide nuts 38 for rear lid locking screws. Consequently, since the nuts 38 are covered with the protector 14, the nuts 38 are less easily seen from the outside. It is possible to fix the rear lid section 12 and the case main body section 10 without spoiling an external appearance. The rear lid section gasket 70 is inserted between the rear lid section 12 and the case main body section 10. Therefore, it is possible to secure waterproof performance by strongly tightening the rear lid section gasket 70 with the nuts 38 and screws 58.

A reason why the nuts 38 and the screws 58 are used to fix the rear lid section 12 and the case main body section 10 in this embodiment is explained. In general, when a component made of a resin material is fixed by the screws 58, a method of cutting screw holes in the resin component or a method of casting the nuts 38 in a mold and molding the nuts 38 during molding of the resin component is adopted. However, although the former method is acceptable if the screws 58 having a large size are adopted, when thin screws are adopted, it is difficult to form screw holes including "cut screws" having necessary strength. When there is a purpose of reducing size and weight of a device as in the embodiment of the invention, the screws 58 having a small size need to be adopted. However, when it is attempted to open, in the resin component, screw holes corresponding to such small screws 58, it is conceivable that the screw holes do not have a sufficient hold or a "stripped crew" state occurs when screws are inserted into and pulled out from the screw holes only several times. When the latter casting molding is adopted, a problem involved in a reduction in size occurs.

It is technically difficult to accurately arrange the small nuts 38 corresponding to the thin screws 58 during the molding. This is likely to cause an increase in costs. Therefore, in this embodiment, spaces for housing the nuts 38 are provided in the case main body section 10 and, on the other hand, spaces for housing the screws 58 are provided in the rear lid section 12. A method of holding and fixing the rear lid section gasket 70 between the case main body section 10 and the rear lid section 12 using the nuts 38 and the screws 58 in an assembly process is adopted. By adopting such a configuration, it is possible to reduce weight and size of the biological information measurement device 2 in a simple assembly process and secure waterproof performance. The assembly process is explained below.

In this way, the case main body section 10 and the protector 14 are configured as separate bodies without being integrated. Therefore, the protector 14 can be a component that the user can easily attach and detach. For example, the user is enabled to purchase the protectors 14 having different designs and attach the protectors 14 to the biological information measurement device 2 by himself or herself. Consequently, the user can "dress up" the biological information measurement device 2 by himself or herself.

In the biological information measurement device 2, as explained above, it is important to apply pressure to the wrist 6. This stress is controlled by a tightening force of the band attached to the device. Therefore, an attachment angle of the band to the device is extremely important. However, the angle is varied depending on the size of the wrist 6 of the user.

Figure 6:
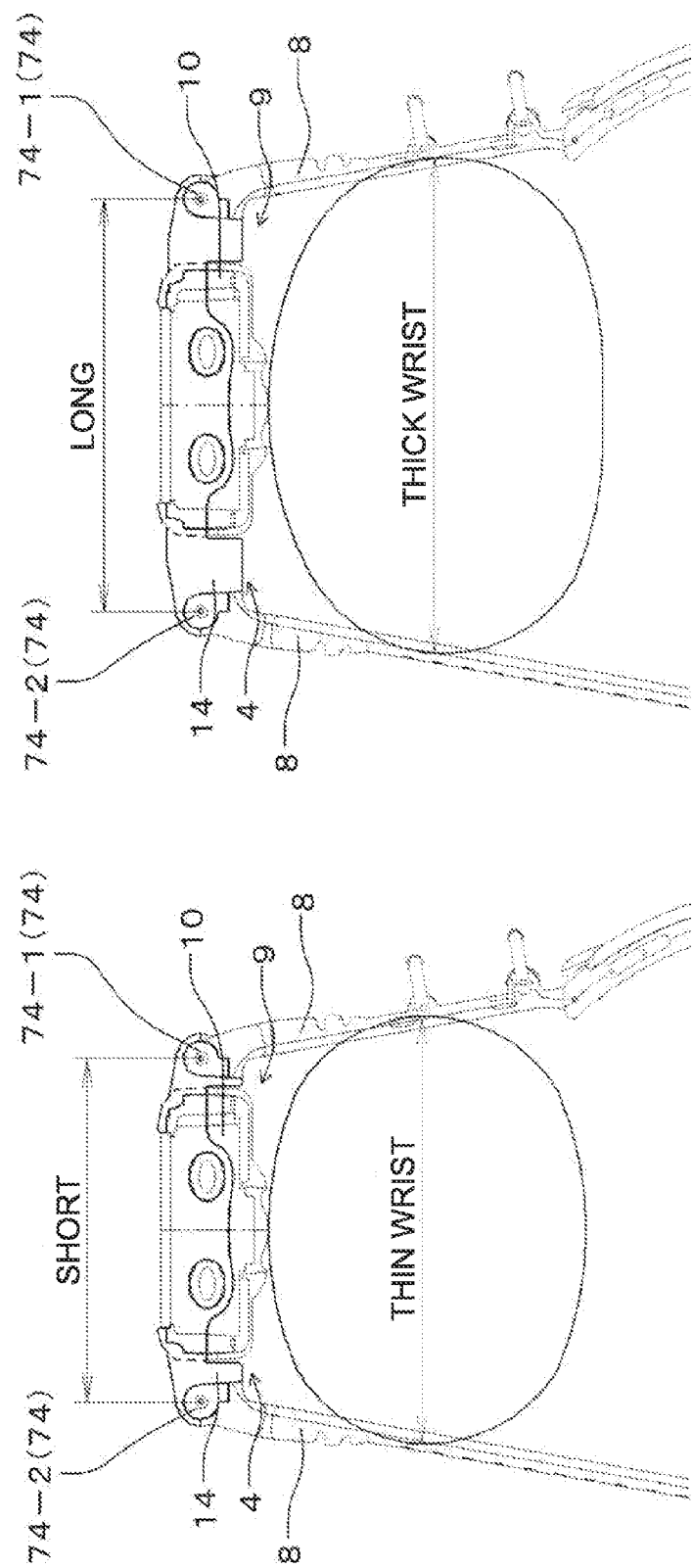
FIG. 6 is a side view showing the biological information measurement device according to the embodiment.

FIG. 6 is a side view showing the biological information measurement device 2 according to this embodiment. In FIG. 6, the engaging sections 74 for connecting the band sections 8 to the device main body 4 are arranged in the protector 14 rather than in the case main body section 10. With such a configuration, for example, as shown in FIG. 6, if the protectors 14 having different distances between a first engaging section 74-1 and a second engaging section 74-2 are prepared and the protector 14 suitable for the thickness of the wrist 6 of the user is incorporated in the armor case 9, it is possible to provide a device more suitable for the user.

In the biological information measurement device 2 in this embodiment, as light blocking structures, the protector 14, the panel cover 28, the light-guide control section 34, and the outer side 12-2 of the rear lid section are adopted. The light blocking structures are multiply provided in this way to suppress intrusion of external light into the biological-information sensor section used in the embodiment. To effectively use the light blocking structures, a preferred arrangement of the light blocking structures in this embodiment is explained with reference to FIG. 4B and FIGS. 5A and 5B. Referring to FIGS. 4B and 5A, the inner edge of the panel cover 28 is arranged further on the center line side of the armor case 9 than the inner edge of the protector 14. With such an arrangement, it is possible to form a structure for blocking external light without spoiling visual recognition of characters, marks, and the like printed or stamped on the panel cover 28.

Referring to FIG. 5B, on a surface parallel to a C-C cross section of the biological information measurement device 2, i.e., a cross section parallel to a 12 o'clock-6 o'clock direction in a state in which the biological information measurement device 2 is mounted on the wrist, the center of the detection window 72 is arranged in substantially the same position as the center of the windshield 18. In other words, on this cross section, the detection window 72 is arranged in substantially the center of the rear lid section 12. The outer side 12-2 of the rear lid section rising to substantially the same position as a projecting position of the detection window 72 is arranged to surround the detection window 72. Preferably, the projecting position of the outer side 12-2 of the rear lid section is lower than the projecting position of the detection window 72 by 1 mm. That is, the outer side 12-2 of the rear lid section is closer to the case main body section 10. With such a configuration, when the biological information measurement device 2 is mounted on the wrist 6 of the user, it is easy to arrange the detection window 72 in the center of the wrist. Compared with a deflected arrangement of the detection window 72, external light, which causes noise during biological information measurement, less easily intrudes into the biological information measurement device 2. Since the outer side 12-2 of the rear lid section is arranged such that the projecting position of the outer side 12-2 of the rear lid section is lower than the projecting position of the detection window 72, the detection window 72 can be configured to be capable of blocking unnecessary external light while sufficiently coming into contact with the human body.

This transparent window is desirably formed in a lens-like spherical shape. This shape can apply pressure suitable for sensing to the skin of the wrist 6. Further, the spherical shape is desirably formed in a shape rising from a position one stage deeper from the edge of the window to set the center of the spherical shape to slightly project from the outer periphery of the window. A projection amount of the center of the spherical shape is closely related to biological information measurement. Therefore, it is necessary to strictly manage the projection amount. In a boundary between a transparent section and a nontransparent material section of the rear lid, an edge molded by a transparent material projects slightly more than a nontransparent section. The projection amount can be managed by managing the transparent edge and a projecting section (the center). That is, the projection amount is determined in primary molding (molding of the transparent material) and fluctuation in the projection amount due to the influence of secondary molding can be eliminated. Therefore, accuracy of the projection amount is markedly improved.

Figure 7:
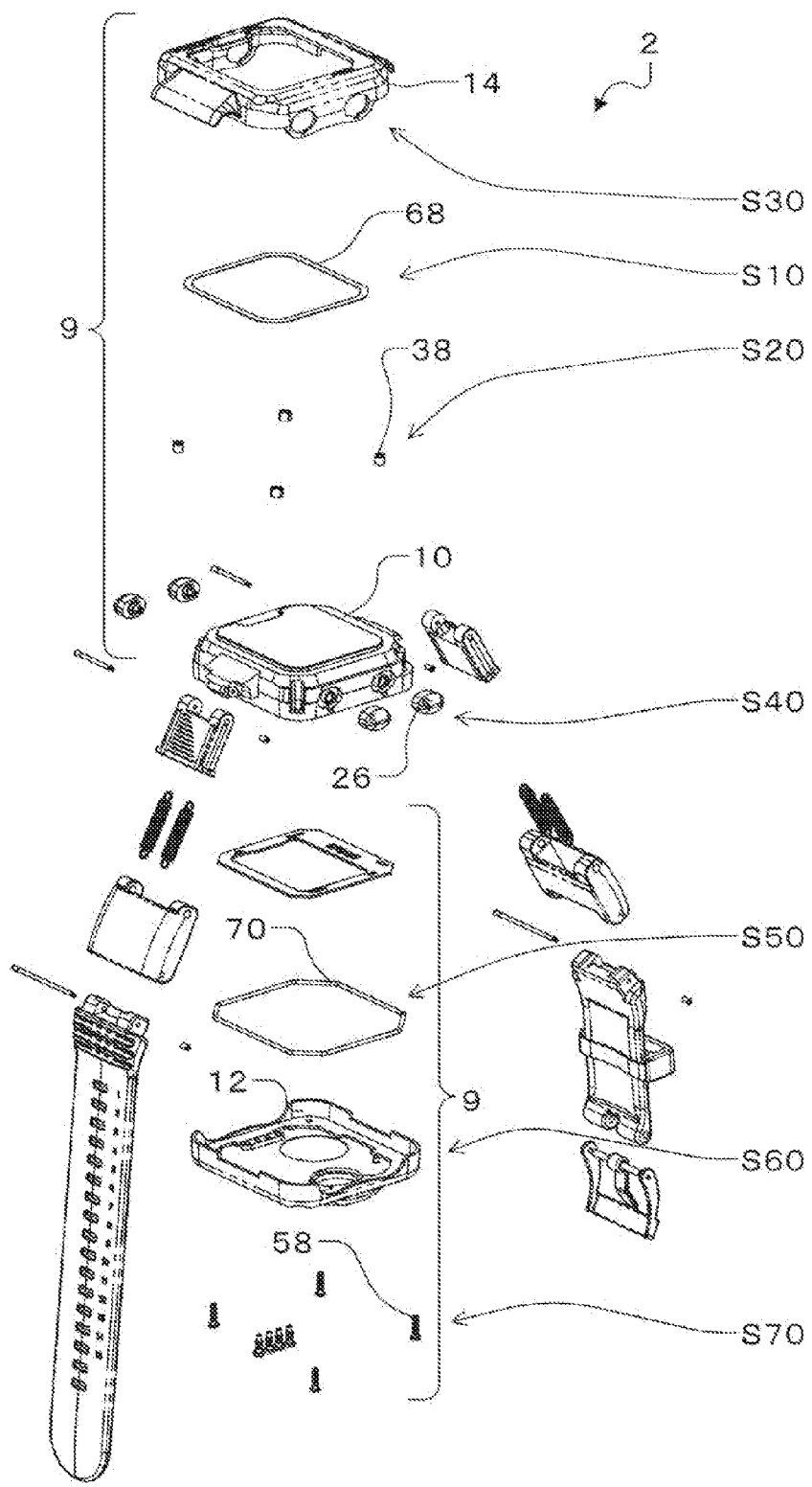
FIG. 7 is an exploded view showing the biologic information measurement device according to the embodiment.

A method of assembling an armor of the device main body 4 of the biological information measurement device 2 is explained below. FIG. 7 is an exploded view showing the biological information measurement device 2 according to this embodiment. First, in step S10, a double sided tape 68 is stuck to the upper surface of the case main body section 10.

Subsequently, in step S20, the nuts 38 are set in four places of the case main body section 10.

In step S30, the protector 14 is fit in the case main body section 10 such that the protector 14 is fixed to the case main body section 10 by the double sided tape 68 stuck to the case main body section 10.

In step S40, the operation buttons 26 are attached to the case main body section 10 using an E-ring holder.

In step S50, the rear lid section gasket 70 is set around the opening section 20 of the case main body section 10.

In step S60, the rear lid section 12 is attached to the case main body section 10 to close the opening section 20 of the case main body section 10.

In step S70, the screws 58 are tightened into the nuts 38 to fix the rear lid section 12 to the case main body section 10.

This assembly method does not include work for incorporating the glass gasket in the past in the case main body section 10 and work for pushing glass into the case main body section 10. Therefore, a large jig, a certain degree of expertise, and the like necessary for these kinds of work are unnecessary. Consequently, a load on a manufacturing process is reduced and a reduction in costs and a yield are improved.

The band sections 8 are explained in detail with reference to FIGS. 8A and 8B to FIGS. 18A and 18B.

Schematic Configuration of the Biological Information Measurement Device

Figure 8A:
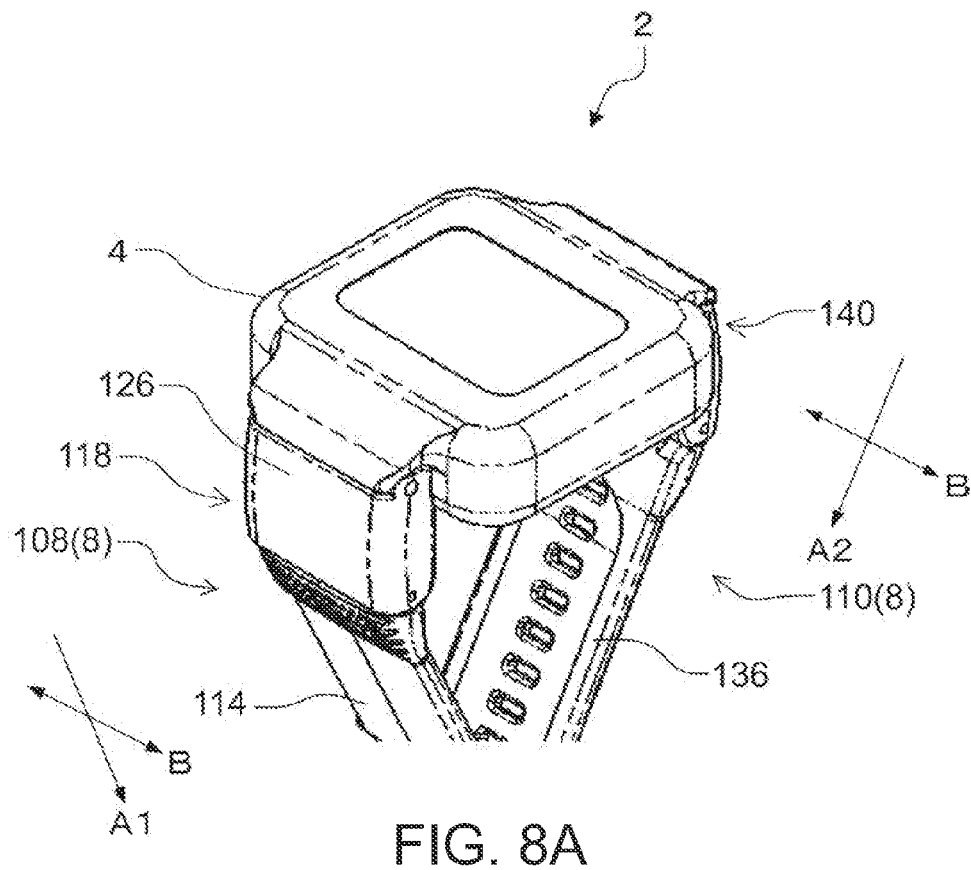
Figure 8B:
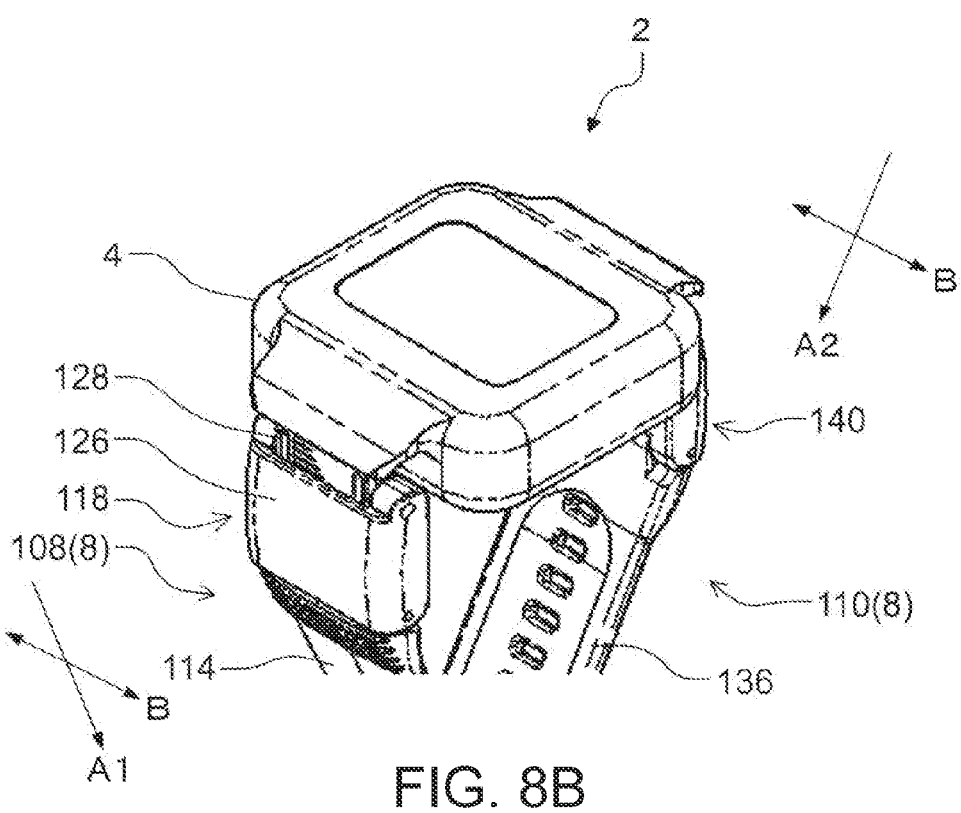
Figure 9A:
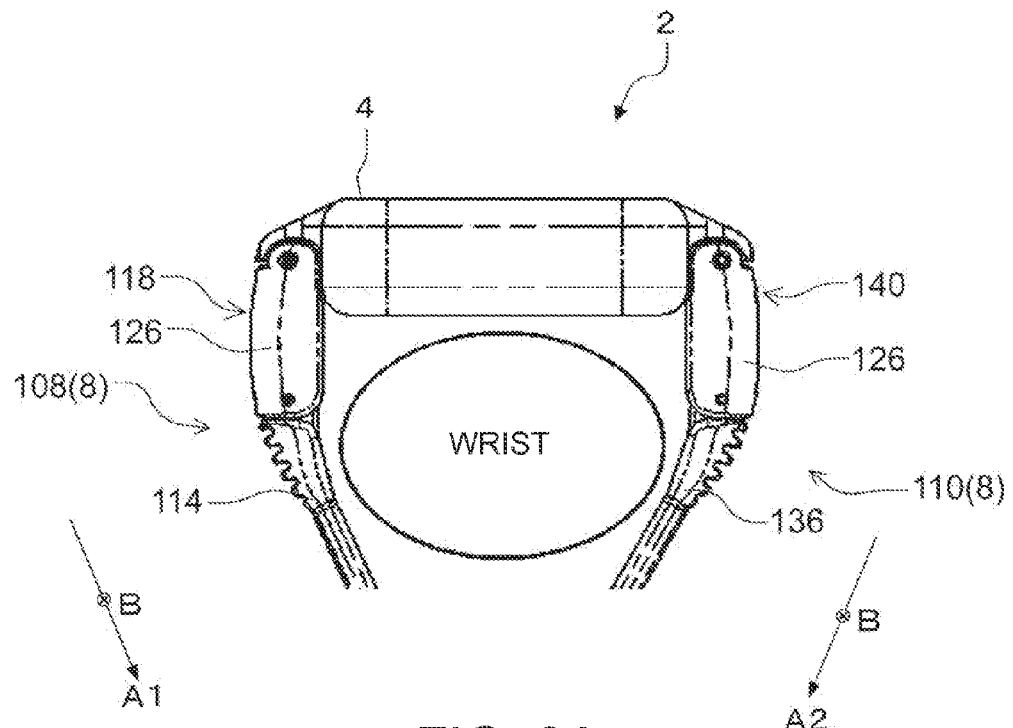
Figure 9B:
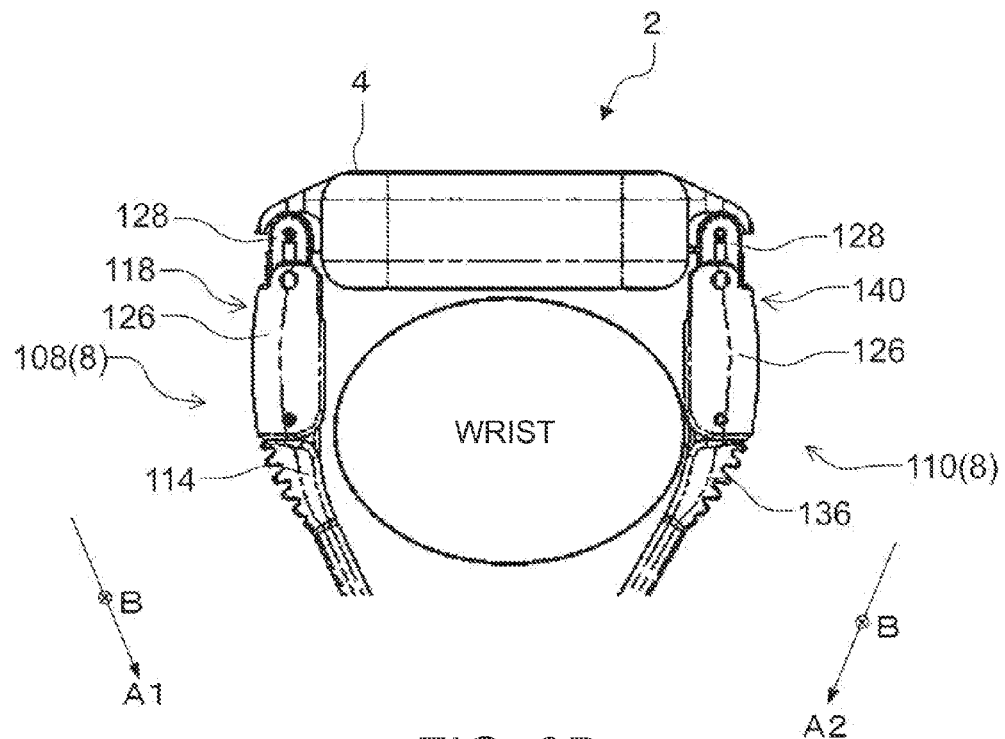
Figure 10:
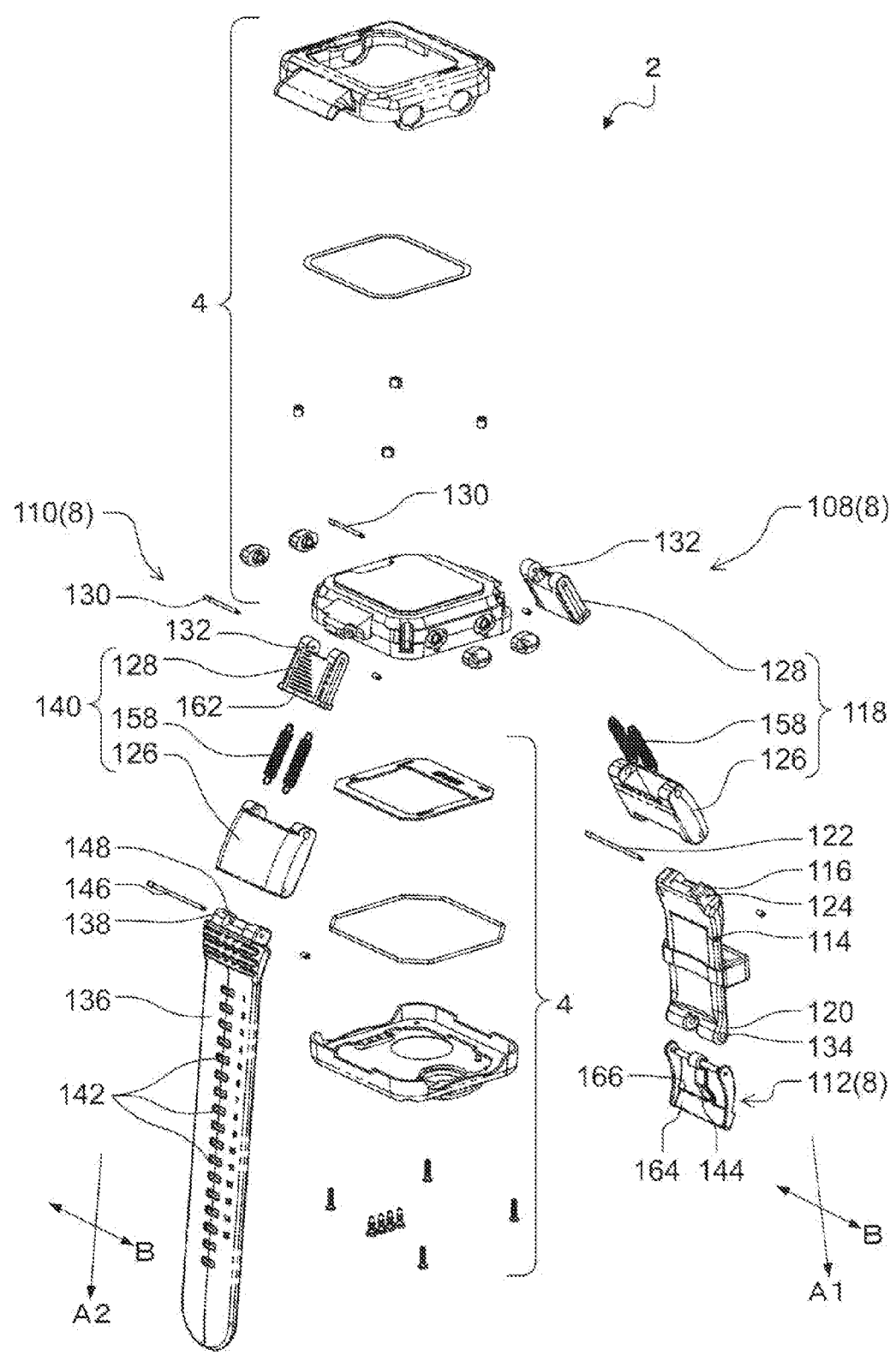
FIG. 10 is an exploded view showing the biological information measurement device according to the embodiment.

FIGS. 8A and 8B are perspective views showing the biological information measurement device 2 according to this embodiment. FIGS. 9A and 9B are side views showing the biological information measurement device 2 according to this embodiment. FIG. 10 is an exploded view showing the biological information measurement device 2 according to this embodiment. Note that FIG. 8A and FIG. 9A show a state of expandable sections 118 and 140 before displacement of a second fitting member 126. FIG. 8B and FIG. 9B show a state of the expandable sections 118 and 140 after the displacement of the second fitting member 126.

Configuration of the Band

The band sections 8 are sections for mounting the device main body 4 on the human body. The band section 8 includes a first band member 108 attached to a lag of the device main body 4 (e.g., in a watch, a lag on the 12 o'clock side), a second band member 110 attached to a lag (e.g., in the watch, a lag on the 6 o'clock side), and a coupling member 112 for coupling the first band member 108 and the second band member 110. The lags are not shown in the figures.

Note that, in the following explanation, in the first band member 108, the device main body 4 side is represented as "one end side" and the coupling member 112 side is represented as "the other end side". Similarly, in the second band member 110, the device main body 4 side is represented as "one end side" and the opposite side of the device main body 4 side is represented as "the other end side".

Configuration of the First Band Member

The first band member 108 includes a band main body 114, a first coupling section 116 and the expandable section 118 formed on one end side (the device main body 4 side) of the band main body 114, and a second coupling section 120 formed on the other end side of the band main body 114. The band main body 114 is a member formed in a flat oblong shape from a urethane or silicon material. The first coupling section 116 includes an insert-through hole 124, through which a spring bar 122 is inserted along a B direction. The expandable section 118 is attached to the band main body 114 via the spring bar 122.

The expandable section 118 is located on one end side with respect to the first coupling section 116 and located in the vicinity of the device main body 4 in the band section 8. The expandable section 118 has flexibility and is formed thicker than the band main body 114 in order to secure strength during expansion and contraction. A below-mentioned first fitting member 128 of the expandable section 118 includes an insert-through hole 132, through which a spring bar 130 attached to the lag is inserted. The expandable section 118 is attached to the device main body 4 via the spring bar 130.

The second coupling section 120 includes an insert-through hole 134, through which a spring bar (not shown in the figure) is inserted along the B direction. The coupling member 112 is attached to the first band member 108 via the spring bar.

Configuration of the Second Band Member

As explained above, one end of the second band member 110 is attached to the lag of the device main body 4. The second band member 110 includes a band main body 136 and a coupling section 138 and the expandable section 140 formed on the device main body 4 side in the band main body 136. Like the band main body 114, the band main body 136 is a member formed in a flat oblong shape from a urethane or silicon material having flexibility.

The band main body 136 includes a plurality of hole sections 142 formed along an extending direction from the device main body 4 of the second band member 110 (a band extending direction of the second band member 110 and an A2 direction in FIG. 10; the same applies below). A below-mentioned projecting bar 144 of the coupling member 112 is inserted through any one of the hole sections 142.

The coupling section 138 and the expandable section 140 respectively have the same configurations as the first coupling section 116 and the expandable section 118. Specifically, the coupling section 138 is formed at one end (the end on the device main body 4 side) of the band main body 136. The coupling section 138 includes an insert-through hole 148, through which a spring bar 146 is inserted along the B direction. The expandable section 140 is attached to the band main body 136 via the spring bar 146. The expandable section 140 is formed at one end (the end on the device main body 4 side) of the second band member 110. The below-mentioned first fitting member 128 of the expandable section 140 includes the insert-through hole 132, through which the spring bar 130 attached to the lag is inserted.

The expandable section 140 is located on one end side with respect to the coupling section 138 and located in the vicinity of the device main body 4 in the band section 8. The expandable section 140 has flexibility and is formed thicker than the band main body 136.

Configuration of the Expandable Section

Figure 11:
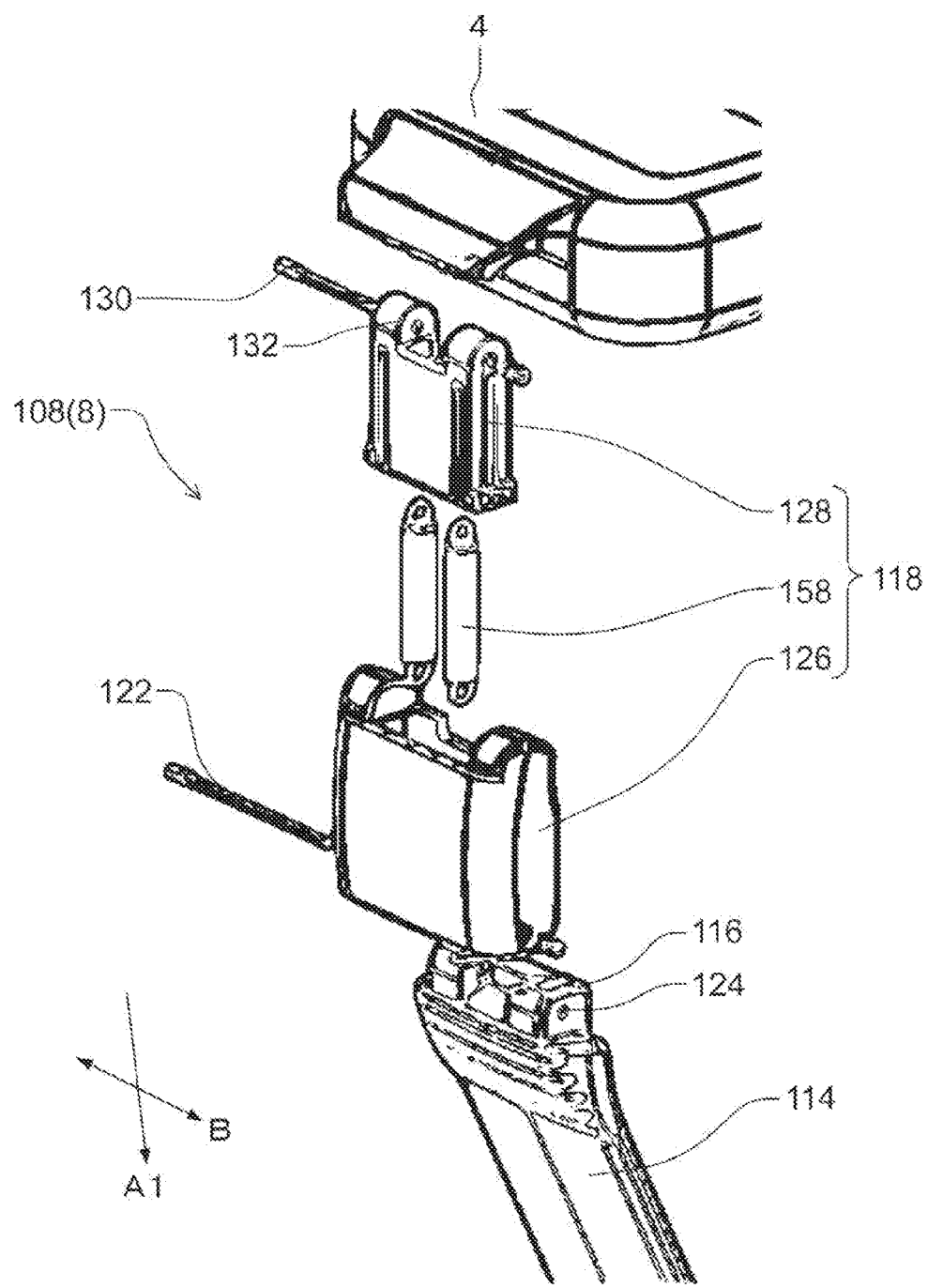
FIG. 11 is an exploded view showing the expandable section according to the embodiment.
Figure 12A:
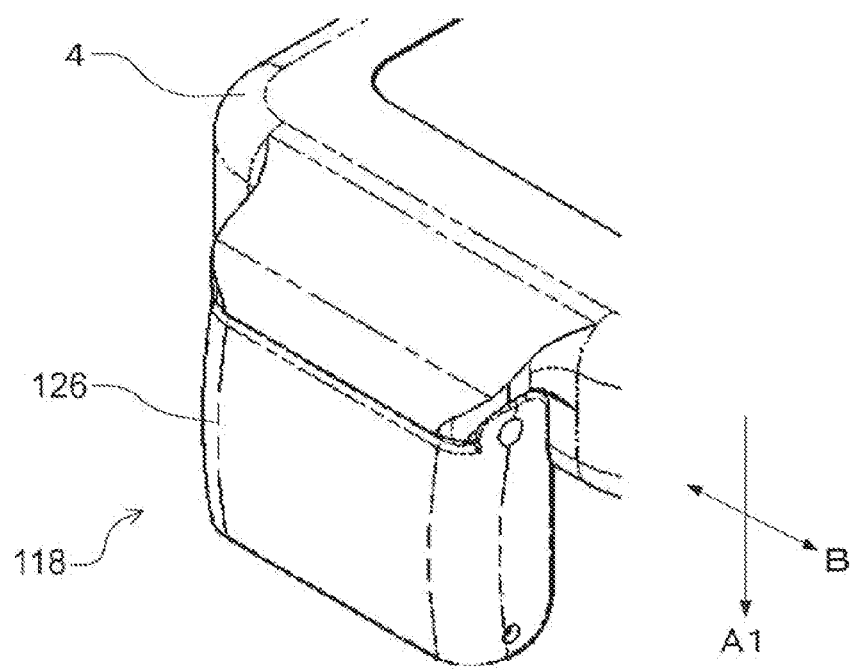
Figure 12B:
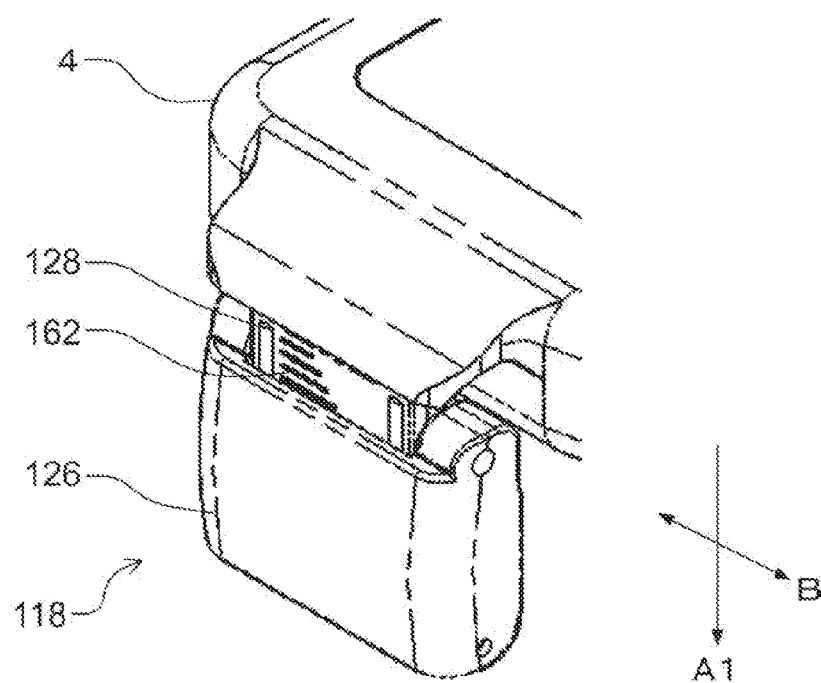

FIG. 11 is an exploded view showing the expandable section 118 according to this embodiment. FIGS. 12A and 12B are perspective views showing expanding and contracting states of the expandable section 118 according to this embodiment. FIGS. 13A and 13B are sectional views showing expanding and contracting states of the expandable section 118 according to this embodiment. Note that FIGS. 12A and 13A show a state of the expandable section 118 before displacement of the second fitting member 126. FIGS. 12B and 13B show a state of the expandable section 118 after the displacement of the second fitting member 126. Note that the expandable section 140 of the second band member 110 has a configuration same as the configuration of the expandable section 118 of the first band member 108. Therefore, explanation of the configuration is omitted.

The expandable section 118 includes the first fitting member 128, the second fitting member 126, and coil springs 158 functioning as urging members. The first fitting member 128 and the second fitting member 126 are members made of metal or synthetic resin. The fitting member 128 has a structure of a male fitting member. The second fitting member 126 has a structure of a female fitting member. Consequently, since the second fitting member 126 on the band section 8 side of the expandable section 118 has the structure of the female fitting member, only the second fitting member 126 of the first and second fitting members 128 and 126 comes into contact with the human body (the skin). Therefore, slidability of the expandable section 118 is high (see FIG. 9B). Since a boundary between the first fitting member 128, which is the male fitting member, and the second fitting member 126 does not come into contact with the human body (the skin), the skin is less easily nipped.

Configuration of the First Fitting Member

Figure 14:
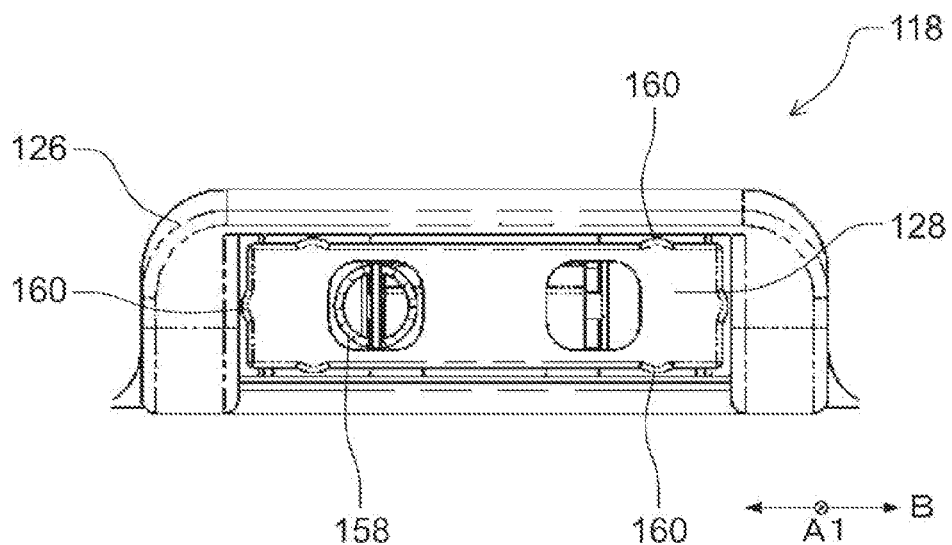
FIG. 14 is a bottom view of the expandable section showing an engagement state of a first fitting member and the second fitting member according to the embodiment.

FIG. 14 is a bottom view of the expandable section 118 showing an engagement state of the first fitting member 128 and the second fitting member 126 according to this embodiment. The first fitting member 128 is a frame-like body configured to displaceably support the second fitting member 126. The first fitting member 128 includes a plurality of convex sections 160 formed along a displacement direction of the second fitting member 126. Consequently, since the displacement of the second fitting member 126 is guided by the plurality of convex sections 160, it is possible to stably displace the second fitting member 126.

Figure 15:
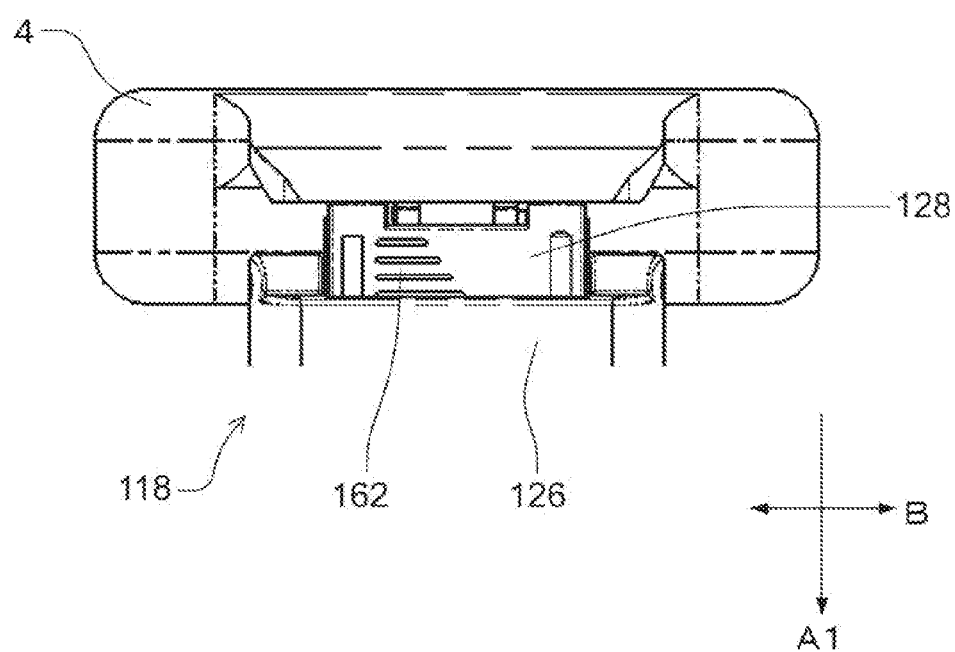
FIG. 15 is a front view showing a display section of the first fitting member of the expandable section according to the embodiment.

FIG. 15 is a front view showing a display section 162 of the first fitting member 128 of the expandable section 118 according to this embodiment. The first fitting member 128 includes the display section 162 on the upper surface thereof. The display section 162 is formed along an A1 direction. In the display section 162, a scale indicating a proper displacement range of the second fitting member 126 is added to the display section 162. Consequently, since it is possible to check a displacement amount of the second fitting member 126 using the display section 162, it is possible to confirm, with reference to the displacement amount, that a proper tensile force acts on the band section 8 and the device main body 4 is mounted on the human body with appropriate pressure. Specifically, two points (not shown in the figure) indicating the proper displacement range may be added to the display section 162. If the end on the device main body 4 side of the second fitting member 126 is located within the range indicated by the two points, it may be considered that the proper tensile force is acting on the band section 8.

Configuration of the Second Fitting Member.

As shown in FIGS. 12A and 12B and FIGS. 13A and 13B, the second fitting member 126 is displaced relatively to the first fitting member 128 along the A1 direction to adjust the length dimension of the band section 8 and pressure applied to the human body by the device main body 4. That is, the second fitting member 126 has a function of causing a tensile force to act on the band section 8 and bringing the device main body 4 into close contact with the human body.

Configuration of the Coil Springs

The coil springs 158 urge the second fitting member 126 with respect to the first fitting member 128 in a direction approaching the device main body 4 side (the opposite direction of the A1 direction). As shown in FIG. 11, a pair of the coil springs 158 is provided along the A1 direction. As explained above, the coil springs 158 are housed in the first and second fitting members 128 and 126. One ends of the coil springs 158 on the device main body 4 side are locked by the end of the spring bar 130 and the other ends are locked by the spring bar 122.

In a state in which the second fitting member 126 is not displaced (the state shown in FIG. 12A), as shown in FIG. 13A, the coil springs 158 are housed in the first and second fitting members 128 and 126 in a state in which the coil springs 158 are slightly contracted by the ends of the spring bar 130 and the spring bar 122. Therefore, even in this state, an urging force for maintaining the state, i.e., an urging force for urging the second fitting member 126 to the device main body 4 side acts on the second fitting member 126. When drawing springs are used as the coil springs 158, it is unnecessary to displace the coil springs 158 during assembly. Therefore, an assembly process for the band section 8 is further facilitated.

When the second fitting member 126 is displaced in the A1 direction (changes to the state shown in FIG. 12B) from this state, as shown in FIG. 13B, the coil springs 158 are expanded by the spring bar 130 and the spring bar 122 displaced according to the displacement of the second fitting member 126. Since the spring bar 130 is fixed, the urging force greatly acts on the second fitting member 126. The second fitting member 126 is about to return to the state shown in FIG. 13A.

Therefore, when the band members 108 and 110 are coupled via the coupling member 112, if a wearer releases the hand from the band members 108 and 110, the second fitting section 126 displaced in the A1 direction by a tensile force of the wearer is about to be displaced in the opposite direction of the A1 direction by the urging force of the coil springs 158. Consequently, the second band member 110 coupled to the first band member 108 by the projecting bar 144 of the coupling member 112 is drawn in the opposite direction of the A1 direction along the first band member 108, whereby the band section 8 is additionally tightened according to pressure applied to the human body by the device main body 4. Therefore, the device main body 4 is brought into close contact with the human body with appropriate pressure.

Configuration of the Coupling Member

The coupling member 112 is a member made of metal or synthetic resin functioning as a buckle configured to couple the first band member 108 and the second band member 110. The coupling member 112 is attached to the second coupling section 120. As shown in FIG. 10, the coupling member 112 is formed in an arcuate shape to extend along the wrist 6 such that a cross section of the coupling member 112 along the A1 direction has a predetermined curvature.

The coupling member 112 includes a fixing member 164 and the projecting bar 144. A substantially rectangular opening section 166, through which the second band member 110 is inserted, is formed substantially in the center of the fixing member 164.

A concave section (not shown in the figure), in which the distal end of the projecting bar 144 is housed, is formed on the opposite side of the first band member 108.

As a general-purpose coil spring 158, there are a drawing spring for drawing and extending a spring formed by densely winding a coil and a pushing spring for pressing a spring formed by non-densely winding a coil. In the drawing spring, since the coil is usually in a close contact state, torsional stress due to coil adhesion is generated even in a no-load state. This is generally called initial stress. Therefore, unless a certain degree of a load is applied, the drawing spring is not displaced in a load direction. A load at the time when the drawing spring starts to move in the load direction resisting the initial stress is generally called initial tension. On the other hand, in the pushing spring, since the coil is wound non-densely, the initial stress is extremely small unlike the drawing spring. Therefore, the initial tension for displacing the pushing spring in the load direction is extremely small. Such characteristics of the drawing spring and the pushing spring are compared in FIG. 16.

Figure 16:
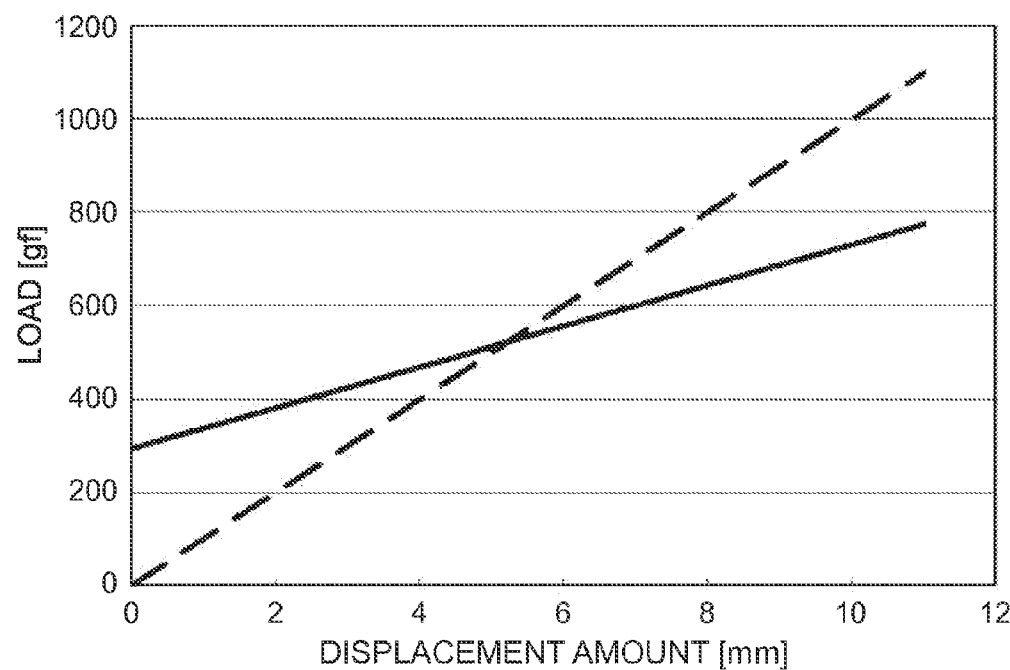
FIG. 16 is a diagram showing a difference between characteristics in a pushing spring and a drawing spring.

FIG. 16 is a diagram showing a difference between the characteristics in the pushing spring and the drawing spring with a displacement amount plotted on the abscissa and a load plotted on the ordinate. Note that, in the actual coil spring 158, there are maximum values for enabling displacement of the coil spring 158. However, to simplify the explanation, the coil spring 158 having infinite length is assumed.

A relation between the displacement amount and the load in the drawing spring (a solid line) is represented by a straight line, an intercept of which is the load equivalent to the initial tension as explained above. On the other hand, a relation between the displacement amount and the load in the pushing spring (a broken line) is represented as a straight line passing the origin because the initial tension is extremely small and can be approximated as nearly zero. In a region where the displacement amount is small (a region where the displacement amount is equal to or smaller than 5 mm), since the initial tension is present, the drawing spring can apply a larger load with a small displacement amount. Conversely, a displacement amount of the spring due to fluctuation in a load is small. That is, when the drawing spring is used, it is possible to apply a necessary load to the device main body 4 or the human body with a small displacement amount. At the same time, since a displacement amount of the spring is small when a load from the outside such as an inertial force is applied to the device main body 4, for example, during exercise, it is possible to stably fix the device main body 4 to the human body even during exercise. Further, since a large load can be applied to the device main body 4 with a small displacement amount, it is possible to reduce the size of the expandable section 118.

Further, it is possible to reduce the influence of load fluctuation by appropriately setting an initial load and a spring constant of the drawing spring. Preferably, the magnitude of the initial load is magnitude equivalent to a load suitable for measurement of biological information. With such a configuration, it is possible that the load suitable for measurement of biological information is already applied when the coil spring 158 starts to be displaced.

It is preferable that the magnitude of the initial load is smaller than the load suitable for measurement of biological information. With such a configuration, since the coil spring 158 starts to be displaced before the load suitable for measurement of biological information is applied to the device main body 4, the expandable section 118 moves according to the operation by the user. The user can easily visually grasp the movement of the band section 8 to be set within the range of the display section 162. Therefore, convenience for the user is improved.

It is preferable to set a spring constant such that the gradient of the graph in FIG. 16 decreases. By setting the spring constant in this way, it is possible to reduce a spring displacement amount due to body movement even during exercise and stably fix the device main body 4 to the human body.

Figure 17:
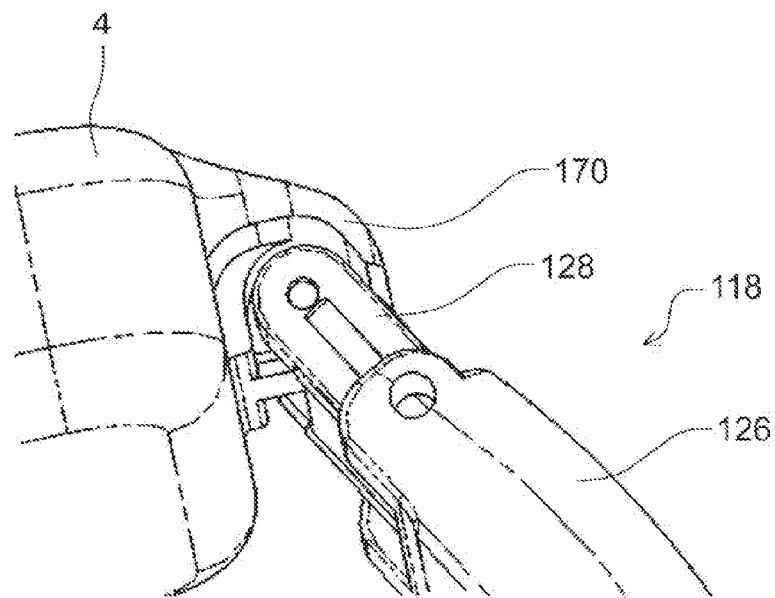
FIG. 17 is a perspective view showing a stopper of a device main body according to the embodiment.

FIG. 17 is a perspective view showing a stopper 170 of the device main body 4 according to this embodiment. The device main body 4 in this embodiment includes stoppers 170 for respectively limiting pivoting of the band members 108 and 110 with respect to the device main body 4. Consequently, since the pivoting of the band members 108 and 110 with respect to the device main body 4 is limited by the stoppers 170, an impact on a part (e.g., glass) of the rear surface of the device main body 4 due to a fall or the like is reduced. The expandable section 118 is configured to be pivotable within a range specified by the stopper 170. Therefore, it is possible to fix the device main body 4 to a user having different thickness of the wrist 6.

According to this embodiment, in the biological information measurement device 2, the case main body section 10 and the windshield 18 in the general structure are integrated. Therefore, it is possible to eliminate a leakage along contact surface of moisture and high-pressure gas in a contact surface section between the case main body section 10 and the windshield 18 and a penetration leakage of the moisture and the high-pressure gas that leak penetrating through an internal texture of a windshield gasket.

Consequently, it is unnecessary to take into account, for example, rigidity design for securing a waterproof property of the contact surface section between the case main body section 10 and the windshield 18. Therefore, it is possible to maintain reduction in size, thickness, and weight of the biological information measurement device 2 and improve waterproof performance. By using the biological information measurement device 2, it is possible to remarkably expand scenes in which biological information of the user can be measured. It is possible to provide an electronic device that can be carried in activities in water such as swimming and walking under water. Further, since reductions in size and weight can be realized, it is easy to carry the biological information measurement device 2 all day long.

Since the photo-sensor is used in the pulse sensor section 36, the biological information measurement device 2 can accurately measure a pulse making use of a phenomenon matching characteristics of the photo-sensor in which the reflectance of light is different during expansion and during contraction of a blood vessel.

In addition, in the biological information measurement device 2, when the pulse sensor section 36 is mounted on the wrist 6 of the user and used, a contact state between the pulse sensor section 36 and the wrist 6 is satisfactory.

Consequently, the biological information measurement device 2 can suppress intrusion of light, which causes measurement noise, into the pulse sensor section 36 including the photo-sensor. The biological information measurement device 2 has a suitable configuration in the use of the photo-sensor.

According to this embodiment, when the biological information measurement device 2 is mounted on the human body, the second fitting member 126 is displaced to move relatively to the first fitting member 128, which is supported by the device main body 4, along the band extending direction of the band members 108 and 110. The coil springs 158 arranged between the first fitting member 128 and the second fitting member 126 urge the second fitting member 126 in the opposite direction of the band extending direction. Consequently, since the first fitting member 128 is provided relatively to the movement of the second fitting member 126, it is possible to suppress movement in an unintended direction of the second fitting member 126.

Modification 1

This embodiment is explained with reference to the biological information measurement device 2 mounted on the wrist 6 to measure biological information. However, a mounting part of the biological information measurement device 2 is not limited to this. The biological information measurement device 2 in this embodiment may be configured to be fixed to the body of the user using a band or a supporter suitable for fixing the biological information measurement device 2 to a measurement part of the user such as the upper arm or the chest.

Modification 2

In FIG. 7, the protector 14 is fixed to the case main body section 10 by the double sided tape 68. However, the method of fixing the protector 14 is not limited to this. As the method of fixing the protector 14, as shown in FIG. 4C, opening sections having a shape corresponding to the operation buttons 26 may be provided in the protector 14 to fix the protector 14 using the operation buttons 26. In other words, the operation buttons 26 may be used as the fixing member 164 for the protector 14. Fitting sections having a substantially convex shape or a substantially concave shape may be provided on side surfaces (surfaces substantially perpendicular to the windshield 18 and the detection window 72) of the case main body section 10 or the rear lid section 12 and fitting sections corresponding to the fitting sections may be provided in the protector 14 to fix the protector 14 using the fitting sections. Alternatively, the protector 14 may be fixed by combining any ones of the methods explained above. With such a configuration, it is possible to more surely fix the protector 14. The protector 14 can be fixed using the side surfaces of the biological information measurement device 2 without using the rear surface of the biological information measurement device 2, i.e., the surface of the rear lid section 12 that comes into contact with the human body. Therefore, since it is unnecessary to arrange an unnecessary structure on the measurement surface side for biological information, it is possible to fix the protector 14 while contributing to stable measurement of biological information. Further, when convenience for a "dress-up" by the user is taken into account, it is preferable that a part of the fitting sections of the protector is configured to curve to a peripheral section of the surface of the rear lid section 12 that comes into contact with the human body. With such a structure, it is possible to suppress an influence on biological information measurement while securing easiness of dress-up of the protector 14 by the user himself or herself.

Modification 3

In the embodiment, the rear lid section 12 is described as being configured by the inner side 12-1 of the transparent rear lid section and the outer side 12-2 of the colored rear lid section. However, the rear lid section 12 is not limited to this. The detection window 72 of the rear lid section only has to be transparent with respect to the wavelength of light used for biological information measurement. For example, all the sections including the light-guide control section 34 may be formed of a colored member and only a region surrounded by the light-guide control section 34 or only the detection window 72 may be formed of a transparent member. In this case, it is possible to form the integrated rear lid section 12 by using colored polycarbonate and transparent polycarbonate in combination. When the rear lid section 12 configured in this way is used, an assembly process does not change from the assembly process shown in FIG. 7 and the same effects are attained.

Modification 4

Figure 18B:
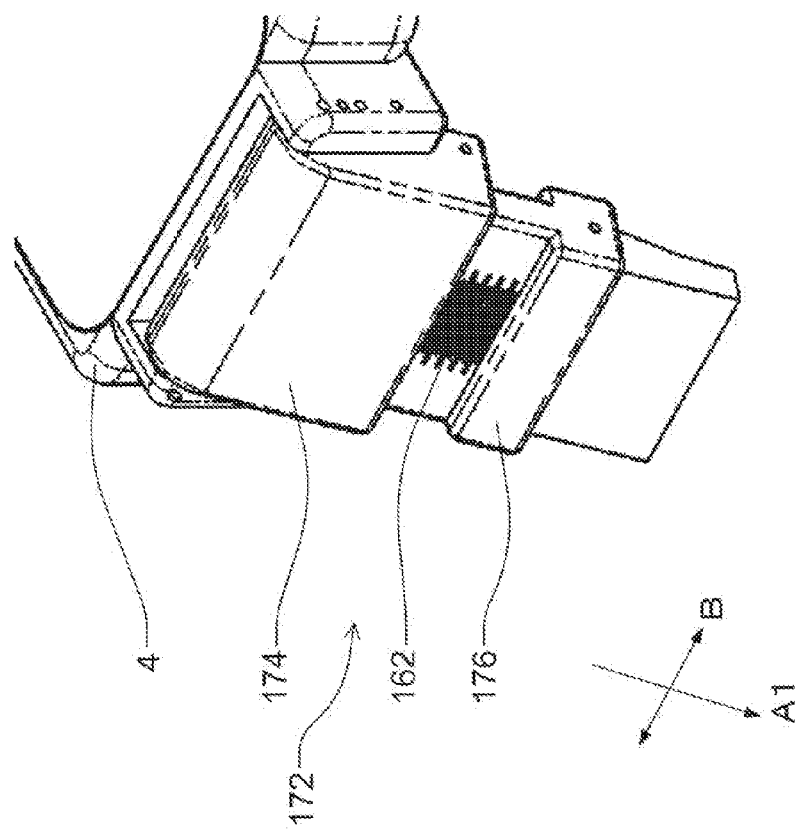
Figure 18A:
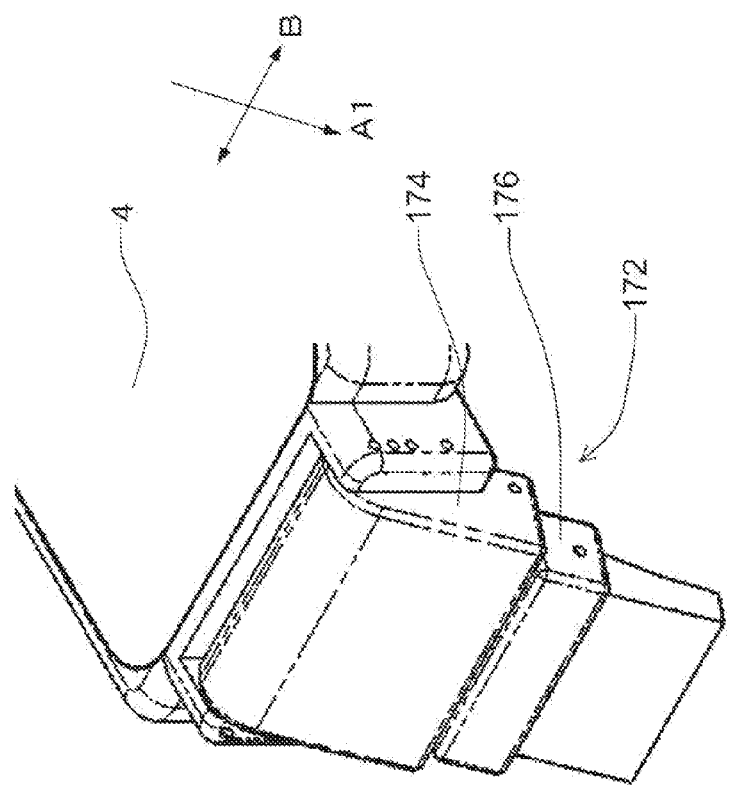

FIGS. 18A and 18B are perspective views showing expanding and contracting states of an expandable section 172 according to this modification. FIG. 18A shows a state of the expandable section 172 before displacement of a second fitting member 176. FIG. 18B shows a state of the expandable section 172 after the displacement of the second fitting member 176.

In the embodiment, the structure of the male fitting member is adopted as the first fitting member 128 and the structure of the female fitting member is adopted as the second fitting member 126. However, the invention is not limited to this. Other configurations may be adopted as long as it is possible to easily specify the position of the second fitting member with respect to the first fitting member. For example, as shown in FIGS. 18A and 18B, the structure of the female fitting member may be adopted as a first fitting member 174 and the structure of the male fitting member may be adopted as the second fitting member 176. The display section 162 may be formed on the second fitting member 176.

Modification 5

In the embodiment, the expandable sections 118 are respectively adopted in the first band member 108 and the second band member 110. However, the invention is not limited to this. The expandable section 118 may be adopted in one of the first band member 108 and the second band member 110.

Modification 6

In the embodiment, the pair of coil springs 158 is adopted in the expandable section 118. However, the invention is not limited to this. One or three or more coil springs may be adopted in the expandable section 118.

Modification 7

In the embodiment, the projecting bar 144 inserted in the hole sections 142 of the second band member 110 is adopted as the coupling section. However, the invention is not limited to this. Other components may be adopted as long as the components can be coupled to the second band member 110. For example, a component coupled to the second band member 110 by holding the second band member 110 may be adopted.

Modification 8

In the embodiment, the band sections 8 are adopted in the biological information measurement device 2. However, the invention is not limited to this. The embodiment may be adopted for a band of a blood-pressure meter, a watch, or the like for measuring biological information such as blood pressure.

Modification 9

The display section 162 serving as a mark in adjusting a load may be provided in the coupling member 112 or may be provide in the first band member 108 or the second band member 110. A scale may be cut in the display section 162. The display section 162 may be configured to notify the user of a load state using different colors stepwise.

What is claimed is:

1. An electronic device that measures biological information, the electronic device comprising:
    a biological-information sensor section configured to measure the biological information; and
    an armor case configured to house the biological-information sensor section, wherein the armor case includes:
    a case main body section; a rear lid section; and
    a gasket provided between the case main body section and the rear lid section, one surface of the case main body section is integrally molded with a windshield and the other surface of the case main body section is formed of a transparent member in which an opening section is formed, and
    the rear lid section is attached to the other surface of the case main body section to close the opening section and at least a part of the rear lid section is formed of a transparent member; and
    a protector provided over a top surface and a part of a side surface of the case main body section; the transparent member of the rear lid is surrounded by a light-guide control section protruded along a direction from the rear lid section to the case main body.

2. The electronic device according to claim 1, wherein the armor case is provided with a protector provided over the case main body section for blocking light to cover the case main body section excluding at least the windshield.

3. The electronic device according to claim 2, wherein the protector includes a first engaging section and a second engaging section for engaging the armor case and a band section.

4. The electronic device according to claim 1, further comprising a panel cover having a light transmission area smaller than the windshield in a projection view in a direction from the case main body section to the rear lid section.

5. The electronic device according to claim 1, wherein the rear lid section further includes a detection window, and
the electronic device further comprises a light-guide control section configured to extend from the rear lid section to the case main body section and block light formed around the detection window.

6. The electronic device according to claim 1, wherein the rear lid section is formed by two-color molding.

7. The electronic device according to claim 5, wherein at least a part of the detection window is formed to project in a direction from the case main body section to the rear lid section.

8. The electronic device according to claim 1, wherein the biological-information sensor section includes a photoelectric sensor.

9. The electronic device according to claim 3, wherein the band section includes:
    a first band member and a second band member attached to a device main body of the electronic device; and
    a coupling member provided at an end on an opposite side of the device main body in the first band member and configured to couple the first band member and the second band member,
    at least one of the first band member and the second band member includes an expandable section configured to expand and contract along a band extending direction, which is an extending direction from the device main body, and
    the expandable section includes:
    a first fitting member located on the device main body side;
    a second fitting member provided to be displaceable with respect to the first fitting member along the band extending direction; and
    an urging member housed in the first fitting member and the second fitting member and configured to urge the second fitting member in an opposite direction of the band extending direction.

10. The electronic device according to claim 9, wherein one of the first fitting member and the second fitting member includes a display section configured to display a displacement amount of the second fitting member.

11. The electronic device according to claim 9, wherein one of the first fitting member and the second fitting member includes a convex section formed along a displacement direction of the second fitting member.

12. The electronic device according to claim 9, wherein one of the first fitting member and the second fitting member is a male fitting member and the other is a female fitting member.

13. The electronic device according to claim 9, wherein the expandable section is configured to be pivotable around a fitting section between the device main body and the first fitting member.

14. The electronic device according to claim 9, wherein the expandable section includes a drawing spring.

15. The electronic device according to claim 9, wherein the device main body comes into contact with a human body and measures the biological information.

16. The electronic device according to claim 15, wherein the device main body includes a stopper configured to limit pivoting of the first fitting member with respect to the device main body.

17. The electronic device according to claim 2, wherein the protector is detachable from the case main body section.

18. The electronic device according to claim 2, wherein light transmitting regions respectively provided in the case main body section, the rear lid section, and the protector through which the inside of the electronic device can be seen, are larger in the order of the case main body section, the protector, and the rear lid section.

19. The electronic device according to claim 2, wherein the protector is fixed to the case main body section after the rear lid section is attached to the case main body section.

20. The electronic device according to claim 9, wherein rotation of the first band member and the second band member are kept within a predetermined range to prevent the first band member and the second band member from spreading wide when the electronic device is removed from a user.

* * * * *